US008404640B2

(12) United States Patent
Dwinell et al.

(10) Patent No.: US 8,404,640 B2
(45) Date of Patent: Mar. 26, 2013

(54) METHOD OF DIAGNOSING AND TREATING COLON CANCER

(75) Inventors: Michael B. Dwinell, Elm Grove, WI (US); Priscilla A. Johanesen, Victoria (AU); Michael K. Wendt, Denver, CO (US)

(73) Assignee: MCW Research Foundation, Inc., Milwaukee, WI (US)

( * ) Notice: Subject to any disclaimer, the term of this patent is extended or adjusted under 35 U.S.C. 154(b) by 603 days.

(21) Appl. No.: 12/255,360

(22) Filed: Oct. 21, 2008

(65) Prior Publication Data
US 2009/0105145 A1 Apr. 23, 2009

Related U.S. Application Data

(62) Division of application No. 11/679,258, filed on Feb. 27, 2007, now abandoned.

(60) Provisional application No. 60/777,156, filed on Feb. 27, 2006.

(51) Int. Cl.
*A61K 38/00* (2006.01)
(52) U.S. Cl. .......................................... 514/12; 530/350
(58) Field of Classification Search .................. None
See application file for complete search history.

(56) References Cited

U.S. PATENT DOCUMENTS
2010/0062009 A9 * 3/2010 Chu et al. .................. 424/184.1

OTHER PUBLICATIONS

Verma et al. (Nature 1997, 389: pp. 239-242).*
Amalfitano et al. (Current Gene Therapy 2002, 2: pp. 111-133).*
Pandha et al. (Current Opinion in Investigational Drugs 2000; 1 (1): pp. 122-134).*
Riva CM, vol. 20, pp. 4463-4472, 2000.*
Zeimet et al. (Lancet. Jul. 2003; 4: 415-422).*
Begley DJ, Pharmacol. Therapy, vol. 104(1), pp. 29-45, 2004.*
Misra et al. (J. Pharmacy and Pharmaceutical Sciences, vol. 6(2), pp. 252-273, 2003.*
Brand et al. (Experimental Cell Research, vol. 310, pp. 117-130, 2005).*
Kollmar et al. (Neoplasia, vol. 9, No. 10, pp. 862-870, 2007).*
Kryczec et al. (Am. J. Physiol. Cell Physiol., vol. 292:C987-C995, 2007).*
Brand et al. (Experimental Cell Research, vol. 310, pp. 117-130, 2005), and.*
Agace et al., (2000) Curr. Biol. 10, 325-328.
Amara et al., (1997) Exp. Med. 186, 139-146.
Arya et al., (2003) Curr. Med. Res. Opin. 19, 557-564.
Balzar et al., (1999) J Mol Med. 77:699-712.
Begum et al., (1996) Biochem. Biophys. Res. Commun. 229, 864-868.
Binion et al., (1997) Gastroenterology 112, 1895-1907.
Bleul et al., (1996) J. Exp. Med. 184, 1101-1109.
Cheong et al., (2006) Science. 314:1308-1311.
Christopherson et al., (2004) Science 305, 1000-1003.
Clark et al., (1994) Nucleic Acids Res. 22, 2990-2997.
Derdeyn et al., (1999) AIDS Res. Hum. Retroviruses 15, 1063-1071.
Dwinell et al., (1999) Gastroenterology 117, 359-367.
Dwinell et al., (2001) Gastroenterology 120, 49-59.
Fearon et al., (1990) Cell 61, 759-767.
Garcia-Moruja et al., (2005) J. Mol. Biol. 348:43-62.
Gazitt (2004) Leukemia 18, 1-10.
Gregorevic et al. (2006) Nat Med. 12:787-789.
Hasegawa et al., (1995) Oncogene. 10:1441-1445.
Haviv et al., (2004) Mot. Cancer Ther. 3, 687-691.
Heidemann et al., (2004) Am. J. Physiol Gastrointest. Liver Physiol. 286, G1059-G1068.
Herman et al., (1996) Proc. Natl. Acad. Sci. U.S.A 93, 9821-9826.
Herman et al., (1997) Cancer Res. 57:837-841.
Hiltunen et al., (1997) Int. J. Cancer. 70:644-648.
Isayeva et al., (2006) Gene Ther. 14: 138-146.
Izadpanah et al., (2001). Am. J. Physiol. Gastrointest. Liver Physiol. 280, G710-G719.
Jones et al., (1980) Cell 20, 85-93.
Jordan et al., (1999) J. Clin. Invest 104, 1061-1069.
Jubb et al., (2003) Ann. N. Y. Acad. Sci. 983, 251-267.
Kane et al., (1997) Cancer Res. 57:808-811.
Kang et al., (2005) Breast Cancer Res. 7, R402-R410.
Kimura et al., (2003) Genes Immun. 4, 356-361.
Lenhard et al., (2005). Clin. Gastroenterol. Hepatol. 3, 142-149.
Li et al., (2002) Bioinformatics. 18, 1427-1431.
Loetscher et al., (1998) J. Biol. Chem. 273: 22279-22283.
Muller et al., (2001) Nature 410, 50-56.
Mund et al., (2005) Nucleic Acids Res. 33:e73.
Nagasawa et al., (1994) Proc. Natl. Acad. Sci. U.S.A 91, 2305-2309.
Nagasawa et al., (1996) Nature 382,635-638.
Panis et al., (1990) J. Hepatol. 11, 53-57.
Phillips et al., (2003) Am. J. Respir. Crit Care Med. 167, 1676-1686.
Ponomaryov et al., (2000). J. Clin. Invest 106, 1331-1339.
Rhee et al., (2000) Nature 404, 1003-1007.
Rhee et al., (2002). Nature 416, 552-556.
Robert et al., (2003) Nat. Genet. 33, 61-65.
Robertson (2001) Oncogene 20, 3139-3155.
Scherf et al., (2000) J. Mol. Biol. 297, 599-606.
Schrader et al., (2002). Br. J. Cancer 86, 1250-1256.
Shirozu et al., (1995) Genomics 28, 495-500.
Sidransky et al., (1992) Science 256:102-105.
Smith et al., (2005) Am. J. Physiol. Gastrointest. Liver Physiol. 288, 316-326.
Subramanian et al., (2006) Cancer Res. 66:4319-4328.
Sun et al., (2003) J. Cell Biochem. 89, 462-473.
Tachibana et al., (1998) Nature 393, 591-594.
Wei et al., (2007) Eur. J. Cancer. 43:490-496.
Wendt et al., (2006) Oncogene. 25:4986-4997.
Whitehead et al., (1999). Gastroenterology 117, 858-865.
Winter et al., (2003) Exp Cell Res. 285:50-58.
Wu et al., (2006) Oncogene 25:1832-1840.
Yan et al., (2002) Methods. 27: 162-169.
Zeelenberg et al., (2003) Cancer Res. 63, 3833-3839.

(Continued)

*Primary Examiner* — Laura B Goddard
*Assistant Examiner* — Meera Natarajan
(74) *Attorney, Agent, or Firm* — Quarles & Brady LLP

(57) ABSTRACT

The invention provides a method of diagnosing carcinoma in a patient, the method comprising providing a sample of colorectal cells from a human patient and analyzing the sample for CXCL12 hypermethylation.

4 Claims, 7 Drawing Sheets

OTHER PUBLICATIONS

Zou et al., (1998) Nature 393, 595-599.

Curriculum Vitae for Michael B. Dwinell, Ph.D. Dated Dec. 5, 2011.

Drury, Luke J. et al. "Monomeric and dimeric CXCL12 inhibit metastasis through distinct CXCR4 interactions and signaling pathways." PNAS 108(43): 2011. pp. 17655-17660.

Wendt, MK et al. "Silencing of epithelial CXCL12 expression by DNA hypermethylation promotes colonic carcinoma metastasis." Oncogene 25: 2006. pp. 4986-4997.

Wendt, MK et al. "Epigenetic silencing of CXCL12 increases the metastatic potential of mammary carcinoma cells." Oncogene 27: 2008. pp. 1461-1471.

Tessema, M. "Re-expression of CXCL14, a common target for epigenetic silencing in lung cancer, induces tumor necrosis." Oncogene 29: 2010. pp. 5159-5170.

Wendt, Michael K. et al. "Constitutive CXCL12 Expression Induces Anoikis in Colorectal Carcinoma Cells." Gastroenterology 135: 2008. pp. 508-517.

Horuk, Richard. "Chemokine receptor antagonists: overcoming developmental hurdles." Nature 8: 2009. pp. 23-33.

\* cited by examiner

SEQUENCE LISTING

<160> NUMBER OF SEQ ID NOS: 16

<210> SEQ ID NO 1
<211> LENGTH: 23
<212> TYPE: DNA
<213> ORGANISM: ARTIFICIAL
<220> FEATURE:
<223> OTHER INFORMATION: SYNTHETIC PCR PRIMER

<400> SEQUENCE: 1
ggagtttgag aaggttaaag gtc                                            23

<210> SEQ ID NO 2
<211> LENGTH: 25
<212> TYPE: DNA
<213> ORGANISM: ARTIFICIAL
<220> FEATURE:
<223> OTHER INFORMATION: SYNTHETIC PCR PRIMER

<400> SEQUENCE: 2

-continued ttaacgaaaa ataaaaatag acgat                                    25

<210> SEQ ID NO 3
<211> LENGTH: 24
<212> TYPE: DNA
<213> ORGANISM: ARTIFICIAL
<220> FEATURE:
<223> OTHER INFORMATION: SYNTHETIC PCR PRIMER

<400> SEQUENCE: 3
gagtttgaga aggttaaagg ttgg                                     24

<210> SEQ ID NO 4
<211> LENGTH: 25
<212> TYPE: DNA
<213> ORGANISM: ARTIFICIAL
<220> FEATURE:
<223> OTHER INFORMATION: SYNTHETIC PCR PRIMER

<400> SEQUENCE: 4
taacaaaaaa taaaaataca acaat                                    25

<210> SEQ ID NO 5
<211> LENGTH: 26
<212> TYPE: DNA
<213> ORGANISM: ARTIFICIAL
<220> FEATURE:
<223> OTHER INFORMATION: SYNTHETIC PCR PRIMER

<400> SEQUENCE: 5
gggattaatt tgtttgtttt ttattg                                   26

<210> SEQ ID NO 6
<211> LENGTH: 23
<212> TYPE: DNA
<213> ORGANISM: ARTIFICIAL
<220> FEATURE:
<223> OTHER INFORMATION: SYNTHETIC PCR PRIMER

<400> SEQUENCE: 6
aactacctcc accccacta tat                                       23

<210> SEQ ID NO 7
<211> LENGTH: 25
<212> TYPE: DNA
<213> ORGANISM: ARTIFICIAL
<220> FEATURE:
<223> OTHER INFORMATION: SYNTHETIC PCR PRIMER

<400> SEQUENCE: 7
ggggttttgt tatagggata ataag                                    25

<210> SEQ ID NO 8
<211> LENGTH: 23
<212> TYPE: DNA
<213> ORGANISM: ARTIFICIAL
<220> FEATURE:
<223> OTHER INFORMATION: SYNTHETIC PCR PRIMER

<400> SEQUENCE: 8
aactacctcc accccacta tat                                       23

<210> SEQ ID NO 9
<211> LENGTH: 24
<212> TYPE: DNA
<213> ORGANISM: ARTIFICIAL

```
<220> FEATURE:
<223> OTHER INFORMATION: SYNTHETIC PCR PRIMER

<400> SEQUENCE: 9
aggcacctcc cgaactaaca actt                                          24

<210> SEQ ID NO 10
<211> LENGTH: 23
<212> TYPE: DNA
<213> ORGANISM: ARTIFICIAL
<220> FEATURE:
<223> OTHER INFORMATION: SYNTHETIC PCR PRIMER

<400> SEQUENCE: 10
ccgctaccac ccttcccaca cca                                           23

<210> SEQ ID NO 11
<211> LENGTH: 18
<212> TYPE: DNA
<213> ORGANISM: ARTIFICIAL
<220> FEATURE:
<223> OTHER INFORMATION: SYNTHETIC PCR PRIMER

<400> SEQUENCE: 11
catcccgcgg gtgttcag                                                 18

<210> SEQ ID NO 12
<211> LENGTH: 22
<212> TYPE: DNA
<213> ORGANISM: ARTIFICIAL
<220> FEATURE:
<223> OTHER INFORMATION: SYNTHETIC PCR PRIMER

<400> SEQUENCE: 12
tgttcccaaa tcatcctcca ga                                            22

<210> SEQ ID NO 13
<211> LENGTH: 17
<212> TYPE: DNA
<213> ORGANISM: ARTIFICIAL
<220> FEATURE:
<223> OTHER INFORMATION: SYNTHETIC PCR PRIMER

<400> SEQUENCE: 13
acggccacaa gttcagc                                                  17

<210> SEQ ID NO 14
<211> LENGTH: 21
<212> TYPE: DNA
<213> ORGANISM: ARTIFICIAL
<220> FEATURE:
<223> OTHER INFORMATION: SYNTHETIC PCR PRIMER

<400> SEQUENCE: 14
cgtcgccgat gggggtgttc t                                             21

<210> SEQ ID NO 15
<211> LENGTH: 20
<212> TYPE: DNA
<213> ORGANISM: ARTIFICIAL
<220> FEATURE:
<223> OTHER INFORMATION: SYNTHETIC PCR PRIMER

<400> SEQUENCE: 15
accacagtcc atgccatcac                                               20
```

```
<210> SEQ ID NO 16
<211> LENGTH: 20
<212> TYPE: DNA
<213> ORGANISM: ARTIFICIAL
<220> FEATURE:
<223> OTHER INFORMATION: SYNTHETIC PCR PRIMER

<400> SEQUENCE: 16
tccaccaccc tgttgctgta                                               20
```

METHOD OF DIAGNOSING AND TREATING COLON CANCER

CROSS-REFERENCE TO RELATED APPLICATIONS

This application is a divisional application of U.S. application Ser. No. 11/679,258, filed Feb. 27, 2007 which claims the benefit of U.S. Provisional Application No. 60/777,156, filed Feb. 27, 2006. All applications are incorporated by reference herein.

STATEMENT REGARDING FEDERALLY SPONSORED RESEARCH OR DEVELOPMENT

This invention was made with United States government support awarded by the following agencies: NIH, Grant Number IROIDK062066. The United States government has certain rights in this invention.

BACKGROUND OF THE INVENTION

Chemokines are small chemotactic cytokines, which direct cellular migration through receptor specific interactions on target cells (Arya, M., et al. (2003). Curr. Med. Res. Opin. 19, 557-564). The homeostatic chemokine-chemokine receptor pair CXCL12 and CXCR4 is widely expressed throughout the body (Bleul, C. C., et al. (1996) J. Exp. Med. 184, 1101-1109). CXCL12, formerly known as stromal cell-derived factor-1 (SDF1), is an alpha type 7.8 kDa CXC chemokine (Shirozu, M., et al. (1995) Genomics 28, 495-500). Originally described as a growth factor for bone marrow developing B cells (Nagasawa, T., et al. (1994) Proc. Natl. Acad. Sci. U.S.A 91, 2305-2309), CXCL12 was subsequently characterized as a chemoattractant for T cells and monocytes (Bleul, C. C., et al. (1996) J. Exp. Med. 184, 1101-1109). Genetic ablation of CXCR4 or CXCL12 results in embryonic lethality (Nagasawa, T., et al. (1996) Nature 382, 635-638). Similar embryonic defects in either of those chemokine receptor or chemokine gene deficient animals has revealed roles for CXCR4-CXCL12 signaling in cardiovascular, neuronal, and hematopoietic stem cell development as well as gastrointestinal vascularization (Tachibana, K., et al. (1998) Nature 393, 591-594; Zou, Y. R., et al. (1998) Nature 393, 595-599). Previous studies by our group have established a role for CXCL12 and CXCR4 in gut vascularization, a key process in mucosal immunity and homeostasis (Heidemann, J., et al. (2004) Am. J. Physiol Gastrointest. Liver Physiol 286, G1059-G1068).

In addition to endothelial expression, the cells of the human colonic epithelium also express both CXCL12 and CXCR4 (Jordan, N. J., et al. (1999) J. Clin. Invest 104, 1061-1069; Agace, W. W., et al. (2000) Curr. Biol. 10, 325-328; Dwinell, M. B., et al. (1999) Gastroenterology 117, 359-367.). Moreover, using an in vitro wound healing assay we have shown that non-transformed intestinal epithelial cells migrate across a denuded surface in response to CXCL12, a key component of the rapid healing ability of the mucosal epithelial surface (Smith, J. M., et al. (2005) Am. J. Physiol Gastrointest. Liver Physiol 288, 316-26). The role of CXCL12-CXCR4 signaling in mucosal wound healing is consistent with other physiologic processes utilizing this signaling axis such as organogenesis and immune surveillance. Thus, our data demonstrate an important role for the combined expression of both CXCR4 and CXCL12 by the cells of the mucosal epithelium. More broadly, these processes of epithelial wound healing, enterocyte migration and vascular angiogenesis, which we have shown in healthy gut mucosa, are known to be dysregulated in colorectal cancer as well as chronic inflammatory diseases. Recent evidence indicates that CXCR4 expression by carcinoma cells may also participate in the metastasis of various cancer types including breast, prostate, non-small cell lung, and colon (Muller, A., et al. (2001) Nature 410, 50-56; Sun, Y. X., et al. (2003) J. Cell Biochem. 89, 462-473, 2003; Phillips, R. J., et al. (2003) Am. J. Respir. Crit. Care Med. 167, 1676-1686; Zeelenberg, I. S., et al. (2003) Cancer Res. 63, 3833-3839). Notably, several studies linking chemokine receptor signaling to cancer cell metastasis suggest that aberrant regulation of CXCR4 expression plays an important role in this process (Haviv, Y. S., et al. (2004) Mol. Cancer. Ther. 3, 687-691; Muller, A., et al. (2001). Nature 410, 50-56.). In contrast, studies defining CXCL12 expression in various carcinomas are more limited.

Given the important functional roles and consistent dual expression of both CXCR4 and CXCL12 by human intestinal epithelium (Dwinell, M. B., et al. (1999). Gastroenterology 117, 359-367; Agace, W. W., et al. (2000) Curr. Biol. 10, 325-328) we hypothesized that perturbations in epithelial CXCL12 expression would contribute to colorectal carcinoma disease progression, possibly by allowing carcinoma cells to more readily sense CXCL12 from exogenous sources, aiding metastasis. This novel hypothesis is supported by evidence from developing hematopoietic stem cells exiting the bone marrow, in which a disruption of CXCL12-CXCR4 signaling is required for stem cell mobilization (Christopherson, K. W., et al. (2004) Science 305, 1000-1003; Gazitt, Y. (2004) Leukemia 18, 1-10). Homing and mobilization of hematopoietic stem cells and hematopoietic cancer cells are mirror image processes, utilizing similar signaling pathways and occurring concurrently: circulating cancer cells constitute an ideal target for concurrent treatment with chemotherapy and antilineage-specific antibodies. Leukemia 18, 1-10).

Our data herein suggest that a disruption in CXCR4 autocrine signaling results from the silencing of CXCL12 in human colonic carcinoma cells. We define a mechanism of CXCL12 silencing in human colorectal carcinoma by DNA methyltransferase (Dnmt) enzyme mediated promoter hypermethylation. Consistent with our hypothesis, re-establishment of endogenous CXCL12 expression in colonic carcinoma cells dramatically reduced in vivo metastatic tumor formation. Our data demonstrate a previously unrecognized mechanism of CXCL12 silencing in colorectal carcinoma, which significantly impacted the metastatic properties of those cells. Further, we suggest a new paradigm in which the epigenetic silencing of one arm of the CXCL12-CXCR4 signaling axis promotes tumor cell metastasis.

SUMMARY OF THE INVENTION

In one embodiment, the present invention is a method of diagnosing carcinoma in a patient, the method comprising providing a sample of colorectal cells from a human patient and analyzing the sample for CXCL12 gene hypermethylation or hypermethylation up-stream from the CXCL12 gene wherein hypermethylation of the CXCL12 gene or the CXCL12 up-stream region indicates a diagnosis of colon cancer.

In another embodiment, hypermethylation is observed via PCR analysis of the CXCL12 gene. Preferably, the CXCL12-M and CXCL12-U primer pairs (SEQ. ID NOs 1 and 2) are used in PCR analysis. In another embodiment, primer pairs selected from SEQ. ID NOs 1-16 are used in PCR analysis.

In another embodiment, the CXCL12 gene region between −275 and −35 is examined for hypermethylation. In another embodiment, the CXCL12 gene regions between −60 and −38 or −12 and +1 are examined for hypermethylation. In another embodiment, the CXCL12 up-stream region −1877 to −1581, −1391 to −1231 or −1123 to −899 is examined.

In another embodiment, the present invention is a method of treating carcinoma in a patient, the method comprising administering to the patient a therapeutically effective amount of CXCL12 protein. In one embodiment, the CXCL12 protein is obtained recombinant DNA technique. In another embodiment, the CXCL12 protein is via native protein.

In another embodiment, the present invention is a method of treating carcinoma in a cell, the method comprising administering to the patient a therapeutically effective amount of CXCL12 protein.

In another embodiment, the present invention is a diagnostic array for diagnosing tumors, the array comprising a multi-gene array comprising the CXCL12 gene and at least one gene selected from the group of P15 (CDKNZB), hMLH1 and APC. In another embodiment, the diagnostic array comprises CXCL12, P15 (CDKNZB), hMLH1 and APC genes.

In another embodiment, the present invention is a diagnostic array for diagnosing tumors, the array comprising primers diagnostic for CXCL12 gene hypermethylation.

Other embodiments, features and objects of the present invention will be apparent to one of skill in the art after examination of the specification, claims and drawings.

DESCRIPTION OF THE INVENTION

In General

The present invention provides methods of treating and diagnosing metastatic tumors in patients by analyzing and/or re-establishing endogenous expression of CXCL12 chemokine. CXCL12 expression in a cell is silenced when hypermethylated, promoting the increased metastasis of cancer cells. However, re-establishing normal CXCL12 expression in cancer cells dramatically reduces tumor cell metastasis, allowing CXCL12 to be manipulated for therapeutic, research and diagnostic purposes.

Therefore, one version of the present invention provides a method of diagnosing carcinoma in a patient. The method comprises analyzing a sample of cells from a human patient for CXCL12 expression and determining the amount of DNA hypermethylation of the sample. The hypermethylation reflects the activity of Dnmt family of enzymes, in particular Dnmt1 and Dnmt3b.

Globally, the human genome is hypomethylated. Within specific genes however, there are regions of more methylation. In cancer, those regions may or may not be methylated while still other genes may become methylated. We refer to those genes as "hypermethylated".

Figure 2:
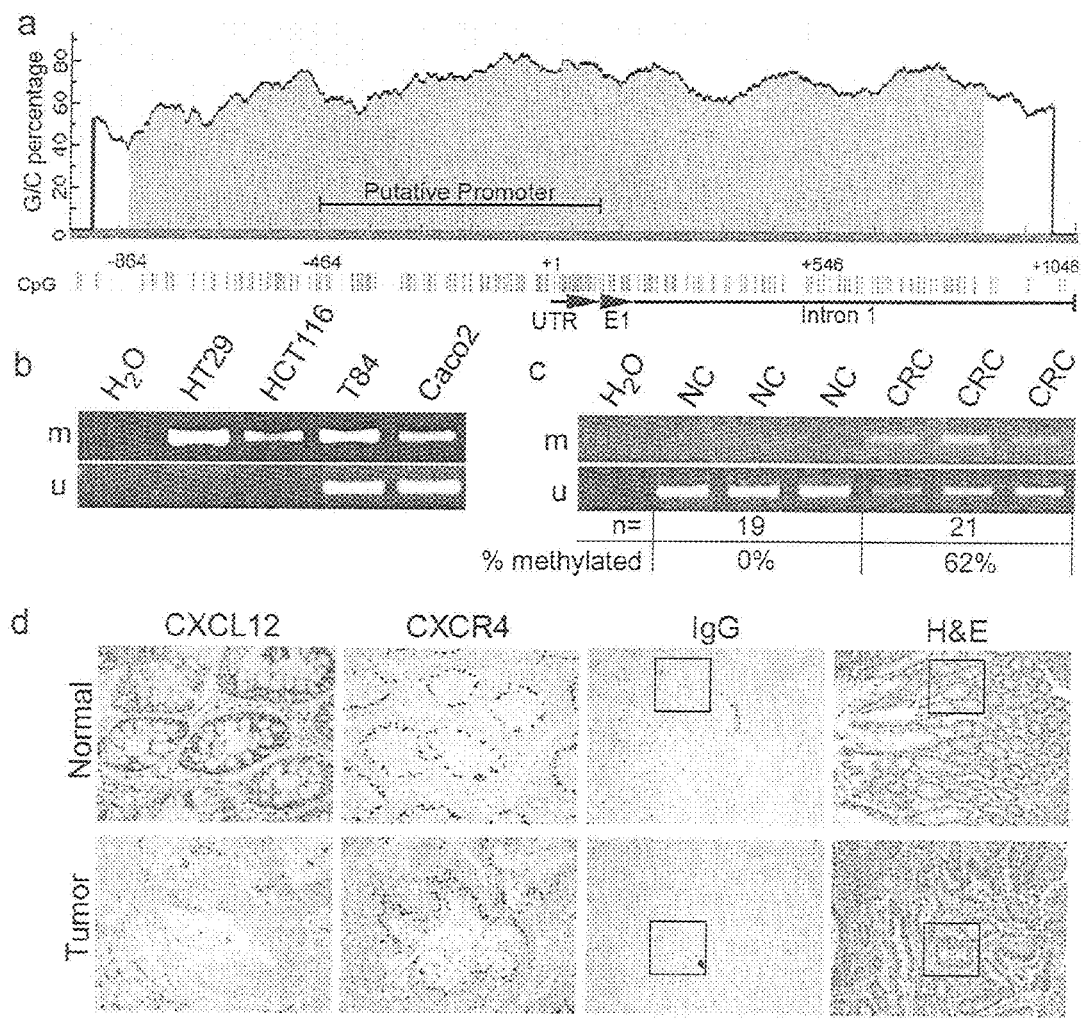
FIG. 2. The CXCL12 promoter region is methylated in human colorectal carcinoma. (A) The 5' region of the CXCL12 gene contains a large CpG island (gray area) encompassing a predicted promoter region, the 5'-UTR and exon one (E1). (B) Methylation-specific PCR indicated the CXCL12 promoter in HT29, HCT116, T84 and Caco2 carcinoma cells was methylated (m). Data from cell lines are representative of 3-5 independent analyses. (C) In contrast, the CXCL12 promoter was homozygous unmethylated (u) in normal human colonic (NC) crypts. The lack of promoter methylation in normal crypt epithelium is representative of 19 separate non-cancerous colonic tissues. Similar to the carcinoma cell lines, several primary human colorectal carcinoma (CRC) tissues showed methylation of the CXCL12 promoter. Data from primary colorectal carcinoma tissues are representative of 21 independent samples and indicate a 62% methylation frequency in CRC relative to 0% observed methylation in NC. (D) Immunohistochemistry of a representative methylated CRC sample from panel (C), indicated CXCL12-specific staining was restricted to normal appearing epithelium and was absent in adjoining cancerous epithelium. CXCR4 staining was consistently observed in normal and cancerous tissues. H&E and IgG control images are shown at 100× magnification with the boxed areas indicating the 400× images shown for CXCL12 and CXCR4 staining on the left-most panels. Data in panel (D) representative of 3 separate methylated CRC specimens.

Any methylation detected with the primers disclosed in Table 1 or to sites disclosed in Table 2 will reflect hypermethylation and is diagnostic of disease. By "hypermethylation" we mean to include methylation detected with the primers disclosed in Table 1 or at the sites disclosed on Table 2. When we refer to hypermethylation of the "CXCL12 gene", we mean the sequence extending from −493 to +168 as a putative promoter region, relative to transcriptional start, +1 (FIG. 2A). Methylation of CpG dinucleotides within this promoter region would be preferable to detect and would include those tabulated in Table 2. Methylation of CpG dinucleotides in any of the four CpG islands detected in the CXCL12 gene and promoter regions is indicative of disease. Additionally, one may also wish to examine up-stream regions of the CXCL12 gene, such as −1877 to −1581, −1391 to −1231, and −1123 to −899, for methylation, as an indication of disease status.

CXCL12-M and CXCL12-U (see Table 1) bind CpG dinucleotides at position −211 within those detailed in Table 2 and within the promoter region. The CXCL12 gene structure is from the sequence obtained from NCBI GenBank database, Accession #AL390792. The reference for characterization of the CXCL12 gene and its promoter region is Garcia-Moruja, C, et al. J Mol. Biol. 348:43-62.

In an alternate version, the present invention provides a diagnostic array for detecting the presence of tumors close to becoming metastatic. While methylation of CXCL12 alone may not be enough to diagnose cancer, diagnostic arrays may be utilized by applying the knowledge that the CXCL12 gene is methylated and silenced. In this instance, for example, adding CXCL12 to a multi-gene array may aid in diagnosing tumors close to becoming metastatic, and thus in need to therapeutic or surgical intervention. Illustrative genes for inclusion in the methylation-specific gene array analysis include the p15CDKN2B, hMLH1 and APC genes:

P15 (CDKN2B): Hernan J G, Civin C I, Issa J P, Collector M I, Sharkis S J, Baylin S B. 1997. Distinct patterns of inactivation of p15INK4B and p16INK4A characterize the major types of hematological malignancies. Cancer Res. 57:837-41.

hMLH1: Kane M F, Loda M, Gaida G M, Lipman J, Mishra R, Goldman H, Jessup J M, Kolodner R. 1997. Methylation of the hMLH1 promoter correlates with lack of expression of hMLH1 in sporadic colon tumors and mismatch repair-defective human tumor cell lines. Cancer Res. 57:808-11.

APC: Hiltunen M O, Alhonen L, Koistinaho J, Myohanen S, Paakkonen M, Marin S, Kosma V M, Janne J. 1997. Hypermethylation of the APC (adenomatous polyposis coli) gene promoter region in human colorectal carcinoma. Int J. Cancer. 70:644-8.

Some level of CXCL12 mRNA expression is typically observed in normal colonic epithelial cells. Therefore, we conclude that in the absence of any CXCL12 mRNA expression, diagnostic methylation analyses determines whether the loss of expression reflects a malignant epigenetic event. The exact level and nucleotides methylated in the CXCL12 gene in colon cancer as it progresses from a benign polyp to an invasive and metastatic tumor has yet to be defined. However, the methylation of a relative few CpG dinucleotides will likely be enough to silence expression of this gene. Further, over-expression of a single Dnmt such as Dnmt1, is likely sufficient to silence CXCL12 and promote tumorigenesis.

Of course, the description set out above is merely of exemplary preferred versions of the invention, and it is contemplated that numerous additions and modifications can be made. Note that further exemplary preferred versions of the invention are described in the appended pages, which are incorporated by reference and constitute a portion of this application.

Diagnosis of metastatic colon cancers. The early detection of colorectal cancer is desired because this cancer can be cured surgically if diagnosed early. To date, several screening methods for colorectal cancer based on the detection of mutated DNA in feces have been reported (Sidransky et al., (1992) Science. 256:102-5; Hasegawa et al., (1995) Oncogene. 10:1441-5). These methods, however, are time-consuming and are not sufficiently sensitive as a nucleic acids in feces are derived from an enormous number and variety of bacteria and normal cells. Accordingly, the proportion of genes derived from cancer cells in stool specimens may be as low as 1% (Hasegawa et al., (1995) Hasegawa et al., (1995) Oncogene. 10:1441-5). Analysis of methylated alleles alleviates some of these concerns as our data indicate that epigenetic silencing of CXCL12 is restricted to neoplastic colonic epithelium and not normal tissue.

The present invention provides early diagnosis of colon cancer by examining the CXCL12 gene from patients for evidence of hypermethylation, preferably achieved using methylation-specific PCR (MSP) to detect the pathologic methylation. As detailed in our Example below, the set of diagnostic MSP oligonucleotide primers disclosed in Table 1 may be used to detect methylation and, thus a cancer diagnosis, of CXCL12 from DNA obtained clinically from patients, preferably from stool specimens, using the Genomic DNA Wizard Kit (Promega, Madison, Wis.) or TRIzol™ (Invitrogen, San Diego, Calif.) according to the manufacturer's instructions. Genomic DNA may be obtained from surgical resection tissue or biopsy tissue obtained during colonoscopic examination.

The following is a sample protocol: DNA (2 µg) is denatured in 0.3M NaOH at 42° C. for 20 min. in a 111 µl reaction volume. To this 1.2 ml of sodium bisulphite solution (4.5 M $NaHSO_3$, 0.02M hydroquinone, and pH 5.0) is added and incubated 16 hrs at 55° C. This reaction is desalted using DNA Purification Wizard (Promega) and the DNA desulfonated in 0.3M NaOH at 37° C. for 20 min. The converted DNA is precipitated at −20° C., overnight in 75% ethanol containing 0.7M ammonium acetate and 0.05 mg/ml of glycogen, reconstituted in 50 µl of water, and 4.0 µl used in each 50 µl MSP PCR reaction using 0.5 µM of specific MSP primers (CXCL12-M and CXCL12-U) (Table 1).

TABLE 1

Primers used for MSP, BSSP, and RT-PCR analyses

| | Application[a] and specificity[b] | Template DNA[c] | Forward Primer (5 to '3') | SEQ. ID NO. | Reverse Primer (5' to 3') | SEQ. ID NO. | Product Size | Anneal Temp |
|---|---|---|---|---|---|---|---|---|
| | MSP | | | | | | | |
| 1 | CXCL12-M | B.S. DNA | ggagtttgagaaggttaaaggtc | 1 | ttaacgaaaaataaaaatagacgat | 2 | 241 bp | 63° C. |
| 2 | CXCL12-U | B.S. DNA | gagtttgagaaggttaaaggttgg | 3 | taacaaaaaataaaaatacaacaat | 4 | 242 bp | 57° C. |
| | BSSP | | | | | | | |
| 3 | CXCL12 | B.S. DNA | gggattaatttgtttgtttttattg | 5 | aactacctccaccccactatat | 6 | 711 bp | 56° C. |
| 4 | CXCL12 | #3 PCR | ggggttttgttatagggataataag | 7 | aactacctccaccccactatat | 8 | 595 bp | 58° C. |
| | RT-PCR | | | | | | | |
| 5 | villin | cDNA | aggcacctcccgaactaacaactt | 9 | ccgctaccaccctteccacacca | 10 | 189 bp | 63° C. |
| 6 | CD45 | cDNA | catcccgcgggtgttcag | 11 | tgttcccaaatcatcctccaga | 12 | 252 bp | 63° C. |
| 7 | eGFP | cDNA | acggccacaagttcagc | 13 | cgtcgccgatgggggtgttct | 14 | 504 bp | 63° C. |
| 8 | GAPDH | cDNA | accacagtccatgccatcac | 15 | tccaccacctgttgctgta | 16 | 452 bp | 63° C. |

[a]MSP, methylation specific PCR; BSSP, bisulfite sequencing PCR.
[b]M, specific for methylated bisulfite converted DNA; U, specific for unmethylated bisulfite converted DNA.
[c]B.S. DNA, bisulfite converted genomic DNA.

The 5' region of the CXCL12 gene contains a large CpG island encompassing a predicted promoter region, the 5'-UTR and exon one. Methylation-specific PCR analysis of DNA from stool, biopsy, or surgical specimens will indicate that the CXCL12 promoter is methylated (m) in colon carcinoma using any CXCL12-M primer. In contrast, the CXCL12 promoter will be homozygous unmethylated (u) in normal human colonic (NC) crypts probed with the CXCL12-U primer. The lack of promoter methylation in normal crypt epithelium is representative of non-cancerous colonic tissues.

Immunohistochemistry of a representative methylated colorectal cancer sample from FIG. 2C, indicated CXCL12-specific staining was restricted to normal appearing epithelium and was absent in adjoining cancerous epithelium. CXCR4 staining was consistently observed in normal and cancerous tissues. We expect only colon cancer to possess methylated CXCL12 alleles and will thus be diagnostic for the disease.

The CXCL12 gene characterization is from the sequence obtained from NCBI GenBank database, Accession #AL390792. The reference for characterization of the CXCL12 gene and its promoter region is Garcia-Moruja C, Alonso-Lobo J M, Rueda P, Torres C, Gonzalez N, Bermejo M, Luque F, Arenzana-Seisdedos F, Alcami J, Caruz A. 2005. Functional characterization of SDF-1 proximal promoter. J Mol. Biol. 348:43-62.

Although we have established the CXCL12-M and CXCL12-U primer set is ideal, we have shown that over 28 CpG dinucleotides in a 600 base-pair region of the human CXCL12 promoter are differentially methylated (Table 2).

sis. These methylation sites have not been analyzed, primarily because they are outside the promoter sequence −275 to −35. However, CpG islands are by definition rich in CpG dinucleotides that may prove useful in enhancing diagnosis.

TABLE 2

Methylation patterns of the CXCL12 putative promoter in CRC cell lines and normal tissues

| CpG number | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Position from +1 | −275 | −258 | −250 | −245 | −235 | −211 | −206 | −199 | −194 | −177 | −166 | −143 | −140 | −131 | −129 | −127 | −115 | −109 |
| HT29 | + | + | + | + | + | + | + | + | + | + | + | + | + | + | + | + | + | + |
| HCT116 | + | + | + | + | + | + | + | + | + | +/− | − | + | + | + | + | + | + | + |
| T84 | + | − | − | − | − | − | − | − | − | − | +/− | − | − | − | +/− | − | − | − |
| Caco2 | − | − | − | − | − | + | + | + | + | + | − | − | − | − | − | − | − | − |
| HIMEC | − | − | − | − | − | − | − | − | − | − | − | − | − | − | − | − | − | − |
| NC3 | − | − | − | − | − | − | − | − | − | − | − | − | − | − | − | − | − | − |
| NC9 | X | − | − | − | − | − | − | − | − | − | − | − | − | − | − | − | − | − |
| NC10 | + | − | − | + | − | − | − | − | − | − | − | − | − | − | − | − | − | − |
| NC11 | + | − | − | − | − | − | − | − | − | − | − | − | − | − | − | − | − | − |
| NC12 | − | − | − | − | − | − | − | − | − | − | − | − | − | − | − | − | − | − |
| NC14 | − | − | +/− | − | − | +/− | +/− | − | − | +/− | − | − | − | − | − | − | − | − |
| PBMC | X | − | − | + | − | − | − | − | − | − | − | − | − | − | − | − | − | − |

| CpG number | 19 | 20 | 21 | 22 | 23 | 24 | 25 | 26 | 27 | 28 |
|---|---|---|---|---|---|---|---|---|---|---|
| Position from +1 | −98 | −92 | −86 | −76 | −74 | −72 | −67 | −62 | −57 | −35 |
| HT29 | + | + | + | + | + | + | + | + | + | + |
| HCT116 | + | + | + | + | + | + | + | + | + | + |
| T84 | − | − | − | − | − | − | − | − | − | − |
| Caco2 | − | − | − | − | − | − | − | − | − | − |
| HIMEC | − | − | − | − | − | − | − | − | − | − |
| NC3 | − | − | − | − | − | − | − | − | − | + |
| NC9 | − | − | − | − | − | − | − | − | − | − |
| NC10 | − | − | − | − | − | − | − | − | − | − |
| NC11 | − | − | − | − | − | − | +/− | +/− | − | X |
| NC12 | − | − | − | − | − | − | − | − | − | − |
| NC14 | − | − | − | − | − | − | − | − | − | − |
| PBMC | − | − | − | − | − | − | − | − | − | − |

+, methylated;
−, unmethylated;
+/− hetrozygous;
X, undetermined.
Direct sequencing of the 595 bp product of BSSP primer set #7 indicated the methylaton status of 28 CpG dinucleotides. The location of each CpG dinucleotide according to the CXCL12 transcriptional start (+1) is indicated. Data is representative of sequence analysis from 2-5 independent B.S.S.P. analyses.

To enhance our diagnostic efficiency, one could design CXCL12-M primers for each of those CpG sites as possible methylation sites indicative of disease prognosis. Furthermore, although our screening of several different methylated CXCL12 primer sets indicated CXCL12-M as optimal, methylation of gene promoters is a processive event. Thus, any additional CpG dinucleotides within the CXCL12 promoter region are candidates for designing methylation-specific primer sets and these may similarly increase diagnostic efficiency.

We have identified 14 particularly promising CpG dinucleotides sites from −60 to −38 and −12 to +1 for diagnostic MSP primers. These 14-sites correspond to −98, −92, −80, −74, −70, −60, −58, −56, −51, −19, −15, −12, −10, and −8 from transcriptional start and include CpG dinucleotides contained within and flanking the essential Sp1/Sp1 transcription factor binding sites from (−58)-(−40) critical for homeostatic CXCL12 expression. Notably, these sites of CXCL12 methylation are within the promoter region encompassed by a large CpG island extending from −840 to +852 (Li, L. C. and Dahiya, R. (2002) Bioinformatics. 18, 1427-1431). We have identified three additional CpG islands further upstream in the CXCL12 gene and extending from −1877 to −1581, −1391 to −1231, and −1123 to −899 have been identified by us (Wendt et al., (2006) Oncogene. 25:4986-97.) and inclusion of methylation primer sets to CpG dinucleotides within those CpG islands may further enhance colon cancer diagnosis.

As CpG islands are portions of the genome with elevated levels of CpG dinucleotides capable of being methylated and impacting gene expression, additional methylation specific primer sets designed to targets in those regions. nC=normal colon. HIMEC=human intestinal microvascular endothelial cells, PBMC=peripheral blood monocytes. HT29, HCT116, T84 and Caco2 are colon cancer cell lines.

The MSP diagnostic approach using DNA obtained from stool specimens could also rely upon the isolation of colonocytes from naturally evacuated feces to increase gene-detecting methods in clinical practice. Using this approach, colonic epithelial cells, which are normally exfoliated in stool will be collected for analysis using Dynabeads Epithelial Enrich™. These beads are uniform, paramagnetic, polystyrene beads (4.5-μm diameter) coated with a mouse monoclonal antibody (mAb Ber-EP4) specific for the glycopolypeptide membrane antigen epithelial cellular adhesion molecule (EpCAM), which is expressed on most normal and neoplastic human epithelial tissues (Dynal, Oslo, Norway). EpCAM is widely expressed along the basolateral membrane in the highly proliferative cells of the intestinal epithelium, from the basal cells to cells throughout the crypts at the basolateral membranes. The development of colonic adenomas has been reported to be associated with increased EpCAM expression and EpCAM over-expression has frequently been demonstrated in colorectal carcinomas (Winter et al., (2003) Exp Cell Res. 285:50-8; Balzar et al., (1999) J Mol. Med. 77:699-712).

DNA would be isolated from the colonic epithelial cells purified from stool, bisulphate converted and MSP analyses using CXCL12-M and CXCL 12-U used to diagnose the pathologic methylation of CXCL12 associated with colorectal cancer development. Patients with adenomas and carcinomas would present with methylated CXCL12. Patients free from cancer would possess only unmethylated CXCL12 alleles.

Fresh tissue samples obtained from the surgically resected specimens of colorectal cancer patients could also be used to obtain genomic DNA and diagnose colorectal cancer using CXCL12-M and CXCL12-U primers with MSP analysis.

Colon carcinomas are comprised of a heterogenous set of genetic and epigenetic changes that culminate in metaplasia and colon cancer. In order to more faithfully diagnose these cancers, researchers are designing DNA microarray tools to diagnose cancer based on acretion of genetic mutations and microsatellite instability, as well as epigenetic, gene methylation and acetylation events. In that instance, addition of primers to identify methylated CXCL12 to such tools will facilitate diagnosis of colon cancer. In methylated DNA microarray analysis, sets of paired oligonucleotides primers, preferably including 3 different CXCL12-M and 3 different CXCL12-U primers diagnostic for CpG site methylation in the CXCL12 gene promoter could be interrogated. (We identified an area of sequence extending from −493 to +168 as a putative promoter region, relative to transcriptional start, +1 (FIG. 2A). Only 3 separate CXCL12-M and CXCL12-U primers, spotted in quadruplicate to the slides, should be needed to provide amplification controls in the microarray analysis.) Oligonucleotides specific to the bisulfite-modified sequence of a portion of the human CXCL12 gene have been designed. To maximize the efficiency and utility of the microarray, primer sets to other methylated alleles known to be silenced in colon cancer, such p16$^{INK4A}$ (Mund et al. (2005) Nucleic Acids Res. 33:e73; Yan et al., (2002) Methods. 27:162-9) will be included in the analysis and will utilize the same printing and analysis strategy.

Each oligonucleotide primer typically is suspended in sodium carbonate buffer (0.1 μmol/L, pH 9.0) to a final concentration of 50 pmol/μl. Approximately 1 nl (100 μm diameter) of each oligonucleotide are then printed to aldehyde-coated glass slides and incubated overnight in a humidified chamber at 22° C., followed by an incubation at 37° C. for 2 hr. Unbound primers are removed by washing with 1% SDS followed by treatment with NaBH$_4$ for 20 min. PCR products of bisulfite-treated DNA are 5'-labeled with the fluorochrome Cy3. Labeled products are resuspended in hybridization solution, denatured at 95° C. for 5 min, followed immediately by a 10 min incubation at 4° C. and applied to the DNA microarray slides. PCR products are allowed hybridize for 3 hr at 42° C., rinsed and sequentially washed 10 min. at 22° C. with 2×SSC-0.1% SDS, 5 min with 0.1×SSC-0.1% SDS, 5 min with deionized H$_2$O, and dried under flowing nitrogen.

Microarray slides are then scanned the fluorescence images analyzed using the appropriate computer software package. For each fluorescent image, the average pixel intensity within each circle was determined and a local background using mean pixel intensity was computed for each spot. Net fluorescence signal was determined by subtraction of this local background from the mean average intensity for each hybridization spot on the microarray. The intensity ratio of M/(M+U), where M is the methylated allele, e.g. CXCL12-M, and U is the unmethylated allele, e.g. CXCL12-U, for each of the oligonucleotides probes was then calculated. Methylated CXCL12 will be detected solely in patients with cancer, while those without will be represented as homozygously unmethylated CXCL12.

Treatment of colon cancer. In a further version, the present invention provides a method of treating carcinoma in a patient by administering to the patient a therapeutically effective amount of CXCL12. In one embodiment, one would administer the CXCL12 gene, thereby directing the patient to express CXCL12. In another embodiment, the administered CXCL12 may be native or recombinant protein.

In a preferred version, tumor cells may be directed to re-express endogenous self-CXCL12 to alleviate metastasis of colon cancer tumor cells. Specifically, gene therapy in which patients with invasive and/or metastatic colon cancers are treated with viral vectors, "naked" plasmid DNA, stable non-viral episome vectors, or mammalian artificial chromosomes encoding CXCL12 will likely be useful in fostering re-expression of the gene and thus diminishing the probability of tumor cell metastasis and survivability. These vectors will ensure that cells lacking CXCL12 will be able to produce physiological levels of the chemokine, from hundreds of picograms per milliliter of serum to 25 nanograms per milliliter of serum.

Advantageously, these gene therapy approaches require the tumor cells themselves produce the chemokine because it is the loss of the normal CXCL12 mRNA expression that allows those cells to functionally respond to distant chemokine gradients produced in other organs. While treatment with methylase inhibitors should also initiate this autocrine signaling path, those therapeutic modalities will likely ignite re-expression of many other silenced genes. Therefore, in a preferred version, recombinant CXCL12 treatments, or therapies targeting the CXCL12 receptor CXCR4, while powerful, will only act to block metastasizing tumor cells and will not engender the more normal functions that CXCL12 re-expression will initiate.

Human Therapy.

1. Generation of CXCL12 expressing rAAV. Preferably, one would supply CXCL12 protein to a patient by constructing a CXCL12 expression vector, preferably using the AAV system. The strength of the recombinant AAV (rAAV) system is that this system uses a vector containing the necessary genes from adenovirus to induce the lytic phase of AAV producing recombinant, replication-deficient AAV virions ready to deliver CXCL12 to colon cancer cells. While the virus retains the ability to ability to deliver its genome to a human cell it is replication deficient outside of the packaging cell lines and is not pathogenic for humans.

Preferably the AAV Helper Free System (Stratagene, La Jolla, Calif.) is used to generate AAV encoding human CXCL12 (AAV-CXCL12). The CXCL12 gene characterization is from the sequence obtained from NCBI GenBank database, Accession #AL390792. As the virus is naturally replication deficient, an unrelated helper adenovirus is typically used to generate AAV virions.

The following plasmids were used to generate CXCL12-encoding rAAV: 1. pAAV-CXCL12, 2. pAAV-IRES-CXCL12eGFP, 3. pAAV-IRES-Renillaluc, 4. pAAVeGFP, 5. pAAV-IRESeGFP, 6. pAAV-IRES-luc and 7. pAAV-IRES-CXCL12Renillaluc. The vectors are typically isolated using the Qiagen MaxiPrep system, purified and cotransfected into HEK293 cells with pHelper and pAAV-RC, which together supply all of the transactivating factors required for AAV replication and packaging. rAAV-CXCL12-encoding viral particles produced by those cells were harvested and used to treat cancer patients or, as a necessary step in clinical trials used to infect tumor bearing mice.

Control experiments completed in vitro have defined the ability of rAAV to modulate HT29 cell proliferation or apoptosis. Thus, HT29 cells were inoculated with titrated $1 \times 10^5$-$1 \times 10^{12}$ viral particles and proliferation and apoptosis measured using [$^3$H]-thymidine or caspace 3/7 assays. Viral invasion efficiency will be assessed by plating $1 \times 10^6$ HT29 cells to tissue culture plates and inoculated with $1 \times 10^5$-$1 \times 10^{12}$ pAAV-IRES-CXCL12-Renillaluc or, as a control, pAAV-IRES-Renillaluc viral particles, washed, and incubated 5 minutes with Dual-Luciferase Reporter assay reagents and luminescence measured using a spectrophotometer. The ability of rAAV-infected cells to produce functional CXCL12 will preferably be assayed using ELISA to detect secreted protein and secondly by chemotaxis of CXCR4-expressing target cells towards infected cells {Wendt, Johanesen, et al. (2006) Oncogene. 25:4986-97. 1374/id}.

2. Treating cancer. Human patients presenting with colorectal cancer, especially late stage metastatic tumors face worsened disease prognosis and decreased life-expectancy. Our data shows that re-expression of CXCL12 dramatically prevents tumor metastasis and that treatment of colonic carcinoma with this chemokine should reverse disease prognosis and increase life-expectancy. CXCL12 gene re-expression in colonic carcinoma will re-establish the autocrine and paracrine communication arc ascribed to normal intestinal epithelium and ablate tumorigenesis and metastasis. The preferred method of treatment will be to use recombinant adeno-associate virus (rAAV) to integrate the human CXCL12 gene coding sequence into carcinoma cells, leading to CXCL12 gene expression and protein secretion.

Recombinant AAV encoding CXCL12 (termed AAV-CXCL12) will preferably be administered in titrated doses, with a range between $1 \times 10^5$-$1 \times 10^{12}$ viral particles suspended in 100 µl volume expected to be optimal, to patients, either as an intravenous or intramuscular injection obtained as on an "out-patient" basis.

Serum levels of CXCL12 will be monitored by obtaining peripheral blood and measuring chemokine levels using enzyme-linked immunoassay (ELISA) as defined below. Thus, patients receiving AAV-CXCL12 injections will demonstrate an increase in circulating CXCL12 chemokine levels, with an expected increase of 5-150 ng/ml blood being obtained. These levels are well tolerated in humans and should have minimal if any side-effects. As an alternative to intravenous or intramuscular injection, patients may receive AAV-CXCL12 via an intratumoral injection, in which case higher gene expression may be encountered. Similarly, AAV-CXCL12 could be administered via colonoscope during endoscopic examination of the adenoma or developing carcinoma could also be used without loss of efficacy.

Patients receiving AAV-CXCL12 should re-express the chemokine gene independent of the epigenetic silencing machinery and thus should maintain production and secretion of CXCL12. This re-expression results in the re-establishment of the healthy CXCL12-CXCR4 autocrine signaling modality of the normal colonic epithelium, limiting the metastatic mobility of those tumor cells. It is expected that administration of AAV-CXCL12 will enhance disease prognosis and increase life-expectancy. It is expected that administration of AAV-CXCL12 will enhance disease prognosis and increase life-expectancy resulting from increased circulating levels of CXCL12 chemokine. Clinically, therapeutic CXCL12 will yield smaller sized tumors that fail to metastasize and establish in ectopic tissues and that will be more amenable to surgical removal. Decreased primary tumor should therefore result in relief from rectal bleeding, abdominal discomfort and constipation that result from colorectal tumors.

3. Mouse studies. Prior to approval to use this gene therapy approach in humans we will use murine models of human colon cancer to verify the utility of the approach. To define the role for SDF1 in tumorigenesis, we require mice which lack a competent immune system, in order to test the hypothesis that alterations in chemokine or chemokine receptor gene expression and functionally alter the severity of disease and death associated with cancer. We are focusing specifically on the role for chemokines in several critical aspects of colon and breast cancer tumorigenesis including survival, invasion and metastasis (movement from tissue to tissue) of those cells. We will be using mice homozygous for the severe combined immune deficiency (SCID) mutation (Prkdc$^{scid}$). These animals are characterized by an absence of functional T and B lymphocytes. We need to use SCID mice as we intend to implant xenografts of human cells into these animals. Implantation and establishment of these xenografts requires that recipient mice not have a functional immune system which would normally remove the foreign, non-self, graft. Host versus graft immune responses require mature T and B lymphocytes which are absent in SCID mice, thereby facilitating engraftment with human tissues.

Three murine models of human colonic carcinoma metastasis will be evaluated. In each, mice harboring colonic carcinomas receive an intramuscular injection of titrated doses of AAV-CXCL12, or as a control AAV-Renillaluc (Wu, Jia, et al. (2006) Oncogene 25:1832-40; Isayeva, Ren, et al. (2006) Gene Ther. 14:138-46; Subramanian, Bui Nguyen, et al. (2006) Cancer Res. 66:4319-28; Gregorevic, Allen, et al. (2006) *Nat. Med.* 12:787-9). A range of viral particles, which we expect from the literature to encompass $1 \times 10^5$-$1 \times 10^{12}$ viral particles suspended in a 100 µl volume of conditioned medium diluted in sterile saline will be assessed. Optimal concentrations of rAAV-IRES-SDF-Renillaluc will be injected 2, 7, 14, 21, or 28 days later and imaged every 4 days following rAAV injection. The impact of the AAV encoded genes on established 2-week old tumors will be monitored in real-time using the biophotonic imaging. Thus, to image tumoricidal impact of AAV-CXCL12, mice will be anesthetized with isoflurane and receive an intraperitoneal injection with D-luciferin [150 mg/kg] and Coelenterazine [100 mg/kg] the substrate for *Renilla* luciferase. Given that mice succumb to 5-week-old hepatic tumors (Wendt, Johanesen, et al. (2006) Oncogene 25:4986-97), changes in actively metastasizing tumor cells 2 and 7 days post-implantation are expected. In addition to in vivo imaging, tumor-bearing mice will also be monitored by measuring body weight and if detectable by palpation, with calipers. Established tumors will lastly be assessed histologically by fixing the tissues in paraformaldehyde, embedding in paraffin, sectioned and stained with hematoxylin and eosin. The following murine model approaches will be used to ascertain the ability of our therapeutic regimens to block tumor metastasis and elicit tumor death.

3a-1. Portal vein injection. In order to assess tumor cell metastasis, SCID mice, 6-8 weeks of age will first be anesthetized with Ketamine (30 mg/kg)/Rhompun (6 mg/kg), the abdomen cleaned with an organic iodine solution will be used to disinfect the skin and opened through a small midline incision. The intestine will then be gently removed to expose the mesenteric blood vessels. One branch of the superior mesenteric vein will then be isolated by separating the connective tissue around the vein with forceps and $1 \times 10^5$ carcinoma cells suspended in a volume of 150 µl of sterile saline injected using a 27 gauge needle and sterile 1-ml syringe. A small piece of sterile sponge applied with gentle pressure will be used to stop the bleeding following injection. The incision was sutured by muscle and skin two layers using synthetic absorbable sutures (3-0 Vicryl). Tumor formation and metastasis in rAAV-CXCL12 and rAAV-Renillaluc control mice will then be monitored every-other day using biophotonic imaging and after day 21 mice will be killed by $CO_2$ asphyxiation and the livers removed, weighed, and fresh frozen fixed for analysis of metastatic tumors using RT-PCR and immunohistochemistry. For histology, mice will be killed by CO2 inhalation thoracotomized and a midline laparotomy made to remove and formalin-fix the lungs, liver and lymph nodes will be removed, flash frozen in liquid nitrogen and analyzed. Some of the 10 experimental or control mice will receive an injection of AMD3100 to assay specificity on tumorigenesis. For in vivo Biophotonic Imaging mice will be weighed and receive an intraperitoneal injection of 150 mg/kg body weight Firefly D-luciferin 5-15 min prior to anesthetization with isoflurane (see Section IV). Mice will be placed into the Lumina In Vivo Imaging System with their nose aligned with the anesthesia manifold and tumors imaged. Tumors will be monitored immediately after injection.

3a-2. Cecal wall xenograft. In order to assess tumor cell metastasis, SCID mice, 6-8 weeks of age will first be anesthetized with Ketamine (30 mg/kg)/Rhompun (6 mg/kg), the abdomen cleaned with an organic iodine solution will be used to disinfect the skin and opened through a small midline incision. The intestinal cecum will then be exposed through a small incision and $1 \times 10^5$ carcinoma cells suspended in a volume of 150 µl of sterile saline injected using a 27 gauge needle and sterile 1-ml syringe. The incisions are then sutured using synthetic absorbable sutures (3-0 Vicryl). Tumor formation in rAAV-CXCL12 and rAAV-Renillaluc control will be assessed using Biophotonic imaging and when necessary to avoid morbidity mice will be killed by $CO_2$ asphyxiation and the livers removed, weighed, and fresh frozen fixed for analysis of metastatic tumors using RT-PCR and immunohistochemistry. For histology, mice will be killed by $CO_2$ inhalation thoracotomized and a midline laparotomy made to remove and formalin-fix the lungs, liver and lymph nodes will be removed, flash frozen in liquid nitrogen and analyzed.

3a-3. Subcutaneous xenograft. Using a traditional protocol we will engraft SCID mice with human carcinoma cells in order to assess changes in primary tumor volume. For those studies, SCID mice 6-8 weeks of age will be anesthetized with Ketamine (30 mg/kg)/Rhompun (6 mg/kg) and $1 \times 10^5$ carcinoma cells injected subcutaneously in each flank. Carcinoma cells will be suspended in sterile PBS and injected in a 100 microliter volume. Tumors will be monitored in vivo using the Biophotonic Imaging Core mice following administration of rAAV-CXCL12 and rAAV-Renillaluc and tumors monitored immediately after injection and 1, 2, 3, 4 and 5 weeks post engraftment. In separate experiments, we will use RT-PCR and immunohistochemistry to define the phenotype and genotype of our established tumors. Thus, on weeks 1, 2, 3, 4 and 5 after injection experimental and control mice will be killed and the tumors excised, measured in three dimensions with calipers and tumor volume calculated using the formula a X b X c, where a equals long length, b equals width and c equals depth. Tumors will then be flash frozen for subsequent RT-PCR and immunohistochemistry analyses. A separate set of experimental or control mice will receive an injection of AMD3100 to assay specificity on tumorigenesis, tumor volume and viability, vascularization, and cancer cell metastasis. As an alternative to ketamine/rhompun, we will use sodium pentobarbital diluted to 60 mg/kg from a 50 mg/ml stock concentration to anesthetize our mice. Pentobarbital will be injected intraperitoneally using a sterile 30×0.5 gauge needle.

4. Measurement of CXCL12. The levels of CXCL12 produced using these treatment modalities will be measured from serum of patients treated for colorectal cancer using enzyme-linked immunoassay (ELISA). In ELISA, polystyrene 96-well plates (Immulon-4, Dynex Technologies Inc.) are coated with murine mAb to human CXCL12 diluted in carbonate buffer, as the capture antibody. Affinity purified biotinylated goat anti-human CXCL12 diluted in PBS, 1.0% BSA and 0.1% Tween-20 is then used as the detection antibody. The second step reagent was horseradish peroxidase-conjugated streptavidin. Bound horseradish peroxidase was visualized with TMB and $H_2O_2$ diluted in sodium acetate buffer, pH 6.0, the color reaction was stopped by addition of 1.2 M $H_2SO_4$ and absorbance was measured at 450 nm. The CXCL12 concentration is then calculated from a standard curve using recombinant human CXCL12 and can detect as little as 50 pg/ml of serum.

5. Additional therapeutic avenues. While rAAV is a powerful approach to therapeutically transfer human genes into tumor cells several alternative approaches are suitable for engendering CXCL12 re-expression and treating colorectal cancer patients.

5a. Naked DNA. Previous immunotherapy studies have defined the acute and long-term toxicities of intradermal vaccination of cancer patients with lethally-irradiated tumor cells transfected by particle-mediated gene transfer (PMGT). Based upon those findings it is plausible that gold particles coated with a DNA plasmid expression vector encoding human CXCL12 DNA (see above) would be delivered to colonic carcinoma cells using helium pressure with a hand held gene delivery device (Madison Wis.). PMGT transfection, unlike retroviral transfection, does not require tumor cells to proliferate in vitro to undergo gene transfer. PMGT physically inserts the DNA without the need for cell surface interaction with viral components or exposure of the patient to viral antigens and is thus minimally pathogenic. Thus, patients with colorectal cancer would receive, on an outpatient basis, particles-coated with plasmids-encoding human CXCL12 delivered via gene gun every $4^{th}$-$7^{th}$ day. Biopsies would be used to assess infiltration of immune effector cells into the injection site. Serum levels of CXCL12 would be defined post vaccination and compared to the pretreatment control.

Coupling CXCL12-encoded plasmid DNA to gold-particles is one approach. Episome, DNA elements that do not combine themselves with the genetic substance of the host DNA and instead become anchored in a reversible manner only to certain support molecules in the nucleus of the cell could also be administered to patients. Thus, colonic carcinoma patients would receive episomes-encoding human CXCL12 to engender subsequent gene expression and CXCL12 production in cancer cells. Alternative approaches using CXCL12 DNA to treat colon cancer patients would use a quaternized chitosan-60% trimethylated chitosan oligomer (TMCO-60%) encapsulating plasmid DNA encoding CXCL12. The benefit of this latter approach is that the TMCO-vector can be ingested, with recent studies demonstrating gene expression in the mucosa of the stomach and duodenum, jejunum, ileum, and large intestine with minimal toxicity.

Mammalian/human artificial chromosomes (HAC) function as an independent minichromosome, and as such these are potentially useful to achieve safe, long-term expression of a transgene. Our patent would allow us to use HAC vectors carrying the human CXCL12 transgene for gene therapy of colorectal cancer using the patients own cells as the vector. To complete this approach we will clone the CXCL12 coding region behind the 12-kilobase villin promoter and introduce the gene cassettes into the 21DeltapqHAC vector, a HAC vector whose structure is completely defined. HAC-CXCL12 would then be introduced into patient tumor cells and levels of the chemokine defined in their serum using ELISA.

5b. Bacteriolytic vectors. Recent understanding of the unique pathology of solid tumours has shed light on the difficult and disappointing nature of their clinical treatment. All solid tumours undergo angiogenesis that results in biological changes and adaptive metabolisms, i.e. formation of defective vessels, appearance of hypoxic areas, and emergence of an heterogeneous tumor cell population. This micromilieu provides a haven for anaerobic bacteria. The strictly anaerobic clostridia have several advantages over other facultative anaerobes such as *salmonella* or lactic acid-producing, Gram-positive, obligate, anaerobic bifidobacteria. Both pathogenic and non-pathogenic clostridia have been demonstrated to specifically colonize and destroy solid tumors. Early trials of non-pathogenic strains in humans had shown plausible safety. Genetic modifications and adaptation of pathogenic and non-pathogenic strains have further created improved features. However, these manipulations rarely generate strains that resulted in complete tumor control alone. Combined modalities of therapies with chemo and radiation therapies, on the other hand, often perform better, including 'cure' of solid tumors in a high percentage of animals. Considering that clostridia have unlimited capacities for genetic improvement, we predict that designer clostridia forecast a promising future for the development of potent strains for tumor destruction, incorporating mechanisms such as immunotherapy to overcome immune suppression and to elicit strong anti-tumor responses. Thus, we envision using *Clostridium novyi*-NT, an attenuated strain of the obligate anaerobe *C. novyi* to selectively infect and partially destroy experimental cancers because of the hypoxic nature of the tumor environment. We will modify *C. novyi*-NT further so that the bacterium expresses and produces functional CXCL12 to further ablate the tumor and prevent metastasis of the cancer. A prokaryotic vector, pUC19-CXCL12 will be transduced into those anaerobic bacteria to generate *C. novyi*-NT-CXLC12 which will then be administered, as in previous studies, intravenously, with $3-5\times10^3$ colony-forming units expected to be beneficial. As *C. novyi*NT works best in combinatorial therapy regimens (Wei et al., (2007) Eur J. Cancer. 43:490-6; Cheong et al., (2006) Science. 314:1308-11) we will administer a single dose of the lipsomal doxorubicin (Doxil) or other liposome-encapsulated chemotherapeutic agents following administration of CXCL12-expressing clostridia. Bacteria will take up residence in the oxygen-free center of the colonic carcinoma solid tumor where they proliferate and produce CXCL12 which can act in a paracrine signaling mechanism to prevent metastasis. Further, the hypoxic environment of the tumor will foster expression of the CXCL12-vector encoded by the bacterium. Addition of angiogenic chemotherapeutic agents such as Avastin will also be used to enhance the tumoricidal effects of *C. novyi*-NT-CXCL12. Similarly, *Salmonella enterica Typhimurim*, and *Bifidobacteria* species will also be transduced with the CXCL12 vector to generate a panel of therapeutic bacteriolytic treatment vehicles.

We believe that CXCL12-CXCR4 expression confers a "health" signal to human gut epithelium. It is possible we can recapitulate this signaling arc through administration, either orally or intravenously, of synthetic or recombinant CXCL12, thereby abolishing the chemotactic signal and preventing tumor metastasis. This approach may also have the added benefit of fostering increased angiogenesis of the primary tumor as we have shown CXCL12 and CXCR4 are critical for endothelial tube formation of human intestinal microvascular endothelial cells in vitro (Heidemann et al., (2005) Am J Physiol Gastrointest Liver Physiol. 286:G1059-68). Similarly, given the expression of CXCR4 on human leukocytes, administration of native CXCL12 may foster immune targeting of the tumor cells and facilitate immune killing of the cancer. Studies in human bearing the CXCL12/SDF1-3'A allele possess higher serum levels of CXCL12 without detrimental effect, and in HIV1+ patients display slowed progression to AIDS. Although recombinant CXCL12 is available commercially its expression in bacterial systems prevents its use clinically. Thus, we would use synthesized CXCL12 chemokine to abolish colon tumors.

5d. CXCR4 receptor agonists. Congruent with our hypothesis that CXCL12 signaling through CXCR4 is a health signal critical for maintenance of the epithelial barrier and prevention of metastatic cancers it is probable that any ligand capable of binding to CXCR4 will be useful as a therapy to prevent tumor metastasis. For example, Loetscher et al have shown (Loetscher et al., (1998) J Biol. Chem. 273:22279-83) that peptides corresponding to the amino-terminal 9 residues of CXCL12/SDF1 can bind to CXCR4 and elicit biological signaling. Other receptor agonists might include trichosanthin (TCS), an active protein component isolated from a traditional Chinese medicinal herb *Trichosanthes kirilowii*, which has been shown to inhibit HIV infection and been applied in clinical treatment of AIDS. TCS has been shown to enhance signaling of several chemokines including CXCL12 and to bind with high affinity to CXCR4 and other chemokine receptors and may prove useful in studies of tumor metastasis. We would expect pharmacologic doses of recombinant or synthetic TCS, administered intravenously or orally (between 1-1000 nM concentration) to prevent tumor metastasis in our mouse model of colorectal carcinogenesis.

EXAMPLES

In General.

Cellular metastasis is the most detrimental step in carcinoma disease progression, yet the mechanisms that regulate this process are poorly understood. CXCL12 and its receptor CXCR4 are co-expressed in several tissues and cell types throughout the body and play essential roles in development. Disruption of either gene causes embryonic lethality due to similar defects. Post-natally, CXCL12 signaling has a wide range of effects on CXCR4 expressing cells, including the directed migration of leukocytes, lymphocytes and hematopoietic stem cells. Recently, this signaling axis has also been described as an important regulator of directed carcinoma cell metastasis. We show herein that while CXCR4 expression remains consistent, constitutive colonic epithelial expression of CXCL12 is silenced by DNA hypermethylation in primary colorectal carcinomas as well as colorectal carcinoma derived cell lines. Inhibition of DNA methyltransferase (Dnmt) enzymes with 5-aza-2'-deoxycytidine or genetic ablation of both Dnmt1 and Dnmt3b prevented promoter methylation and restored CXCL12 expression. Re-expression of functional, endogenous CXCL12 in colorectal carcinoma cells dramatically reduced metastatic tumor formation in mice, as well as foci formation in soft agar. Decreased metastasis was correlated with increased caspase activity in cells re-expressing CXCL12. These data constitute the unique observation that silencing of CXCL12 within colonic carcinoma cells greatly enhances their metastatic potential.

The chemokine receptor CXCR4 has been shown to be expressed on cancer cells and play a significant role in the process of metastasis (Muller, A., et al. (2001). *Nature* 410, 50-56). In addition to this role, CXCR4 signaling is also a key regulator of organogenesis as well as lymphopoiesis and myelopoiesis (Nagasawa, T., et al. (1994). *Proc. Natl. Acad. Sci. U.S.A* 91, 2305-2309; Zou, Y. R., et al. (1998). *Nature* 393, 595-599). In previous studies we and others have defined the concurrent expression of both CXCR4 and CXCL12 by the cells of the human intestinal epithelium (Jordan, N. J., et al. (1999). *J. Clin. Invest* 104, 1061-1069; Dwinell, M. B., et al. (1999). *Gastroenterology* 117, 359-367). We subsequently determined that that signaling axis regulated enterocyte migration (Smith, J. M., et al. (2005) *Am. J. Physiol Gastrointest. Liver Physiol* 288, 316-26), a key process in the establishment and ongoing repair of the healthy mucosal epithelial barrier. Given this dichotomy between the physiologic and pathophysiologic functions of CXCR4, we hypothesized that changes in the constitutive epithelial expression of CXCL12 may play a pivotal role in determining the function for CXCR4 signaling in the human intestinal mucosa. Our results show that in marked contrast to normal colonic epithelium, CXCL12 is absent in several colorectal cancer cell lines and primary carcinoma tissues, while CXCR4 expression is maintained. We defined DNA hypermethylation as a mechanism for CXCL12 gene silencing in colorectal carcinoma. Further, re-establishing endogenous expression of CXCL12 in colonic carcinoma cells profoundly reduced in vivo metastatic tumor formation, reflecting, in part, increased caspase 3/7 activity in those cells. Current models suggest that CXCR4 expression by tumor cells drives those cells to migrate to ectopic sites of CXCL12 expression. Our data add to this paradigm, wherein the epigenetic silencing of constitutive CXCL12 expression in carcinoma cells, elicits a metastatic phenotype enabling tumor cells to pathologically utilize the chemokine system, exacerbating disease.

Given recent evidence demonstrating the pro-metastatic roles of CXCR4-CXCL12 signaling in carcinoma cells, one may have expected over-expression of CXCL12 in carcinoma cells to result in increased metastasis (Muller, A., et al. (2001) *Nature* 410, 50-56; Kang, H., et al. (2005) *Breast Cancer Res.* 7, R402-R410). The inherent differences between exogenous CXCL12 stimulation and endogenous expression of the protein are undoubtedly responsible for our results compared to previous reports examining the role for CXCR4 in colonic tumorigenesis. We propose that exogenous stimulation of cells with CXCL12 is representative of carcinoma cells which do not produce there own CXCL12 and can thus respond to chemokines produced by distal tissue sites, resulting in protumorigenic signaling processes. We believe our stable re-expression model system is more representative of normal in vivo colonic epithelial cells undergoing autocrine and/or local paracrine CXCL12-CXCR4 signaling, participating in the maintenance of the epithelial barrier, a process requiring cellular migration and apoptosis. Directed cellular migration is dependent on a cell responding to a CXCL12 gradient, a process facilitated in leukocytes and metastatic carcinoma cells by the expression of CXCR4. Our prior reports indicate that CXCL12 signaling through CXCR4 is an important regulator of mucosal wound healing by inducing intestinal epithelial cell migration (Smith, J. M., et al. (2005) *Am. J. Physiol Gastrointest. Liver Physiol* 288, 316-26). The CXCL12 migratory response of immune cells is much higher, however, than that of intestinal epithelial cells, an observation consistent with the intrinsic absence of CXCL12 expression in immune cells (Kimura, R., et al. (2003) *Genes Immun.* 4, 356-361). We show herein that similar to immune cells, carcinoma cells lack expression of CXCL12 but maintain expression of CXCR4. These data are consistent with reports indicating the importance of CXCR4-CXCL12 signaling in the homing of cancer cells to sites of metastasis in which CXCR4-expressing tumor cells pathologically follow endocrine CXCL12 chemotactic gradients, enter the vascular or lymphatic circulation, resist apoptosis and actively invade ectopic tissues (Bleul, C. C., et al. (1996) *J. Exp. Med.* 184, 1101-1109; Muller, A., et al. (2001). *Nature* 410, 50-56; Schrader, A. J., et al. (2002). *Br. J. Cancer* 86, 1250-1256). As shown herein, re-establishing CXCL12 expression in carcinoma cells restored the normal epithelial phenotype preventing pathological utilization of this signaling axis, resulting in reduced in vivo metastatic tumor formation.

Physiologic DNA methylation is achieved by the activity of several Dnmt enzymes. The Dnmt3 family of enzymes is believed to act as the de novo-methyltransferases, while Dnmt1 is believed to act as the maintenance methyltransferase. Many lines of evidence challenge these definitive categorizations making it difficult to predict which Dnmt enzyme is responsible for hypermethylation and gene silencing in cancer (Robertson, K. D. (2001) *Oncogene* 20, 3139-3155). CpG island methylation and gene silencing in the absence of Dnmt1 has been shown, in contrast to reports suggesting Dnmt1 is required to maintain CpG methylation (Robert, M. F., et al. (2003) *Nat. Genet.* 33, 61-65; Rhee, I., et al. (2000) *Nature* 404, 1003-1007). Recent evidence suggests that Dnmt1 and Dnmt3b act cooperatively to silence genes in carcinoma (Rhee, I., et al. (2002). *Nature* 416, 552-556). Consistent with this notion, our results are the first to indicate CXCL12 can be pathologically silenced in colorectal carcinoma by Dnmt1 or Dnmt3b enzymes which are markedly over-expressed in those cells relative to normal epithelium. Further, our data strengthen the importance of epigenetic gene regulation in the processes responsible for changes in cell growth in metaplasia, but also tumor cell invasion and metastasis.

The shift to a metastatic cellular phenotype by the epigenetic down-regulation of CXCL12 expression is paralleled by previous reports noting the absence of CXCL12 expression in isolated primary colonic adenomas as well as other carcinoma cell lines (Begum, N. A., et al. (1996) *Biochem. Biophys. Res. Commun.* 229, 864-868). Similarly, renal tumor cells have been shown to display diminished CXCL12 mRNA expression relative to adjacent normal tissue (Schrader, A. J., et al. (2002) *Br. J. Cancer* 86, 1250-1256). Taken together with these studies, our data suggest that silencing the ligand arm of this signaling axis changes the homeostatic autocrine and paracrine CXCR4 signaling to a strictly endocrine communication arc that facilitates metastasis of those carcinomas.

It has recently been shown that methylation specific markers can be used as a non-invasive diagnostic indicator of tumor progression for colorectal cancer (Lenhard, K., et al. (2005). *Clin. Gastroenterol. Hepatol.* 3, 142-149; Jubb, A. M., et al. (2003) *Ann. N.Y. Acad. Sci.* 983, 251-267). The use of CXCL12 as a methylation marker is promising given the strong correlation shown here between methylation, gene silencing, and disease. The effectiveness of CXCL12 in a panel of methylation markers as an indicator of tumor progression, however, remains to be established through a comprehensive assessment of CXCL12 expression and methylation status in primary tissues of known tumorigenic status (Fearon, E. R. and Vogelstein, B. (1990) *Cell* 61, 759-767).

In summary, the homeostatic expression of CXCL12, but not CXCR4, is a target for gene silencing in colorectal cancer, via DNA hypermethylation by Dnmt1 and Dnmt3b. Silencing of this immunosurveillance chemokine likely aids in carcinoma disease progression, as our data indicates that re-establishment of normal CXCL12 expression in colonic carcinoma markedly reduced tumor cell metastasis in vitro and in vivo. These findings are consistent with and expand upon previous data concerning the role of CXCR4 signaling in carcinoma cell metastasis and maintenance of the human colonic epithelium. Our results, together with recent findings emphasizing the importance of CXCR4 signaling in cancer cell migration and invasion, constitute a unique observation that loss of endogenous CXCL12 expression plays a role in the increased metastasis of cancer cells.

Materials and Methods.

Human colorectal carcinoma cell lines. HT29 (HTB-38), HCT116 (CCL-247), Caco2 (HTB-37), T84 (CCL-248) colonic carcinoma cells were purchased from the American Type Culture Collection (ATCC, Rockville, Md.) and maintained as previously described (Smith, J. M., et al. (2005) *Am. J. Physiol Gastrointest. Liver Physiol* 288, 316-26; Dwinell, M. B., et al. (2001) *Gastroenterology* 120, 49-59). Dnmt1, Dnmt3b or Dnmt1/Dnmt3b double knockout HCT116 cells were the kind gift of Dr. Bert Vogelstein (John Hopkins University School of Medicine) and were maintained similarly to wild-type HCT116 cells. In some experiments, carcinoma cells were treated with 5-aza (EMD Biosciences, La Jolla, Calif.) every 24 hr for the indicated number of days.

Human mucosal samples. Colonic epithelium and human intestinal microvascular endothelial cells (HIMEC) were obtained from surgical remnants from colonic resections or carcinoma biopsy in accordance with protocols approved by the Medical College of Wisconsin human research review committee institutional review board. HIMEC samples were isolated as described previously (Binion, D. G., et al. (1997) *Gastroenterology* 112, 1895-1907; Heidemann, J., et al. (2004) *Am. J. Physiol. Gastrointest. Liver Physiol.* 286, G1059-G1068). To isolate colonic crypts the muscularis externa was detached from surgical specimens and the resulting mucosal strips were washed, minced and incubated 90 min at room temperature in PBS containing 3 mM EDTA and 1 µM DTT and the tube was shaken to liberate crypts. The resulting supernatant, containing epithelial crypts, was transferred to a clean centrifuge tube, and the shaking step repeated for a total of four times. Supernatants were combined, filtered through a sterile gauze pad, and the isolated crypt epithelium collected by centrifugation (Whitehead, R. H., et al. (1999). *Gastroenterology* 117, 858-865).

Immunohistochemistry. Full thickness normal colonic specimens were fixed in 4% (w/v) paraformaldehyde (PFA)/PBS overnight as detailed previously (Heidemann, J., et al. (2004) *Am. J. Physiol. Gastrointest. Liver Physiol* 286, G1059-G1068). CXCL12 protein expression in human colonic epithelium was determined using mouse monoclonal antibody (mAb), clone K15C (Amara, A., et al. (1997) *Exp. Med.* 186, 139-146), or murine isotype control mAb (R&D Systems, Minneapolis, Minn.) and visualized using the alkaline-phosphatase anti-alkaline phosphatase method as described by the manufacturer (DAKO, Carpentaria, Calif.) or DAB as described by the manufacturer (Vector Labs, Burlingame, Calif.).

RT-PCR analysis. Total RNA was isolated from cultured cells and colonic crypt epithelium using TRIzol reagent (Invitrogen, Carlsbad, Calif.), DNase treated (Ambion, Austin, Tex.) and 2 µg of total RNA was converted to cDNA via reverse transcription using random priming in a 40 µl volume. CXCL12, CXCR4, and β-actin mRNA transcripts were amplified using previously described PCR primers and conditions (Heidemann, J., et al. (2004) *Am. J. Physiol Gastrointest. Liver Physiol* 286, G1059-G1068; Smith, J. M., et al. (2005) *Am. J. Physiol Gastrointest. Liver Physiol* 288, 316-26). Other PCR analyses were conducted using listed primer pairs and conditions (Table S1). RNA was excluded in cDNA synthesis reactions as a negative control.

CpG island and promoter analysis. A putative promoter region was identified from 10 kb of genomic sequence encompassing the CXCL12 gene (GenBank Ac#AL390792) including 2 kb flanking the gene both 5' and 3'. This sequence was entered into the Genomatix promoter prediction program "Promoter Inspector" (Scherf, M., Klingenhoff, A., and Werner, T. (2000). Highly specific localization of promoter regions in large genomic sequences by PromoterInspector: a novel context analysis approach. *J. Mol. Biol.* 297, 599-606), or into Methprimer for analysis of CpG dinucleotide content and CpG island identification (Li, L. C. and Dahiya, R. (2002) *Bioinformatics.* 18, 1427-1431). CpG islands were defined as regions of DNA greater than 200 bp, containing a guanine/cytosine content greater than 50% and an observed to expected CpG ratio above 0.6.

Methylation Specific PCR and Bisulphite Sequencing PCR. Genomic DNA from cell lines and colonic crypt preparations was isolated using the Genomic DNA wizard kit (Promega, Madison, Wis.) or TRIzol according to the manufacturer's instructions. Genomic DNA was isolated from paraffin embedded carcinoma tissues by deparaffinization followed by Proteinase K digestion, phenol chloroform extraction, and precipitation in ethanol containing sodium acetate and glycogen as a carrier. DNA (2 µg) was denatured in 0.3M NaOH at 42° C. for 20 min in a 111 µl reaction volume. To this 1.2 ml of sodium bisulphite solution (4.5M $NaHSO_3$, 0.02M hydroquinone, and pH 5.0) was added and incubated 16 hrs at 55° C. This reaction was desalted using DNA Purification Wizard (Promega) and the DNA was desulfonated in 0.3M NaOH at 37° C. for 20 min. The converted DNA was precipitated at −20° C., overnight in 75% ethanol containing 0.7M ammonium acetate and 0.05 mg/ml of glycogen, reconstituted in 50 µl of water, and 4.0 µl used in each 50 µl PCR reaction using 0.5 µM of specific MSP primers (Table S1). The same bisulphite-converted genomic DNA was separately analyzed by bisulphite sequencing PCR (BSSP) using semi-nested primers (Table S1). PCR products obtained with these BSSP primers were directly sequenced using Big Dye Terminator v3.1 (Applied Biosystems, Foster City, Calif.).

Immunofluorescence microscopy. HCT116 epithelial cells were plated to glass chamber slides and grown for 3-days in untreated or 5-aza containing media. Cells were stained with mouse mAb specific for CXCL12 (clone #79018.111, R&D Systems) or a nonspecific mouse IgG control antibody (BD Pharmingen, San Jose, Calif.). CXCL12 protein and IgG background staining was visualized using Alexa Fluor 594 conjugated goat anti-mouse antibody (Molecular Probes, Eugene, Oreg.). Nuclei were visualized with a DAPI counterstain.

Immunoblot analysis. For the detection of Dnmt1, Dnmt3b and actin, whole cell lysates were prepared as previously described (Smith, J. M., Johanesen, P. A., Wendt, M. K., Binion, D. G., and Dwinell, M. B. (2005). CXCL12 activation of CXCR4 regulates mucosal host defense through stimulation of epithelial cell migration and promotion of intestinal barrier integrity. *Am. J. Physiol Gastrointest. Liver Physiol* 288, 316-26), and 10 or 25 µg of protein size separated using reducing SDS-PAGE. Equal protein loading was confirmed by Coomassie blue staining. Proteins were electro-transferred to PVDF (Immobilon-P; Millipore, Bedford, Mass.)

for immunoblot analysis in which blots were incubated with goat antibodies specific for human or rat Dnmt1, Dmnt3b or Actin (Santa Cruz Biotechnology, Santa Cruz, Calif.), and visualized with HRP-conjugated donkey anti-goat antibodies (Santa Cruz Biotechnology) and SuperSignal West Pico Chemiluminescent Substrate (Pierce).

Construction of stable epithelial cell lines. HT29 or HCT116 colonic carcinoma cells were transfected with pcDNA3.1 (Invitrogen) encoding the CXCL12a mRNA transcript, or eGFP, using Nova-Fector (Venn Nova, Pompano Beach, Fla.). Stable plasmid integration was selected using G418 sulfate (EMD Biosciences). Stable gene expression was verified by RT-PCR, fluorescence microscopy, or enzyme link immunosorbent assay (ELISA), using a matched antibody pair (R&D Systems).

Leukocyte chemotaxis assay. HT29 or HCT116 cells were plated and grown to confluence in 24-well dishes. Cells were then serum starved for 2 days. Calcein-AM (Molecular Probes) loaded U937 monocytes ($5\times10^5$) were plated to the upper well of a Transwell chemotaxis chamber (5 µm pore size, Corning Costar, Corning, N.Y.), with the serum-starved epithelial monolayers in the bottom chamber. U937-epithelial co-cultures were supplemented with the CXCR4 receptor antagonist AMD3100 (5 µg/ml) or remain untreated as a control. U937 cells were incubated without epithelial cells or, as a separate control, epithelial cells alone, were used to establish constitutive chemotaxis or auto-fluorescence respectively. U937 cells were incubated with epithelial cells for 3 hr and the number of migrated calcein-loaded monocytes in the bottom chamber quantified by fluorescence spectroscopy (Victor Wallac, Perkin Elmer).

SCID mouse portal vein injection. Using protocols approved by the institutional review board of the Mayo Clinic, HT29 colonic carcinoma cells ($1\times10^6$ cells) stably expressing either CXCL12 or eGFP were suspended in a 100 µl volume of sterile PBS and injected into the portal vein of anesthetized eight-week old male SCID mice (cr-Prdkc$^{scid}$, Charles Rivers, Wilmington, Mass.). Prior to injection all cell lines were ~90% viable as assessed by trypan blue exclusion. Mice were allowed to recover and monitored for tumor development. Tumor-bearing mice were weighed and sacrificed by $CO_2$ inhalation. Livers were removed, tumors dissected from normal tissue and the excised tumors weighed. Total RNA or total cell protein was isolated from normal liver and excised tumor tissue using TRIzol or lysis buffer for RT-PCR and immunoblot analyses, respectively.

Soft agar invasion and caspase assays. Equal numbers of cells were plated on a layer of 0.7% agar made up in full growth media, covered with 0.35% warm agar and cultured for two weeks at which point foci were photographed under bright-field microscopy. For caspase assays HT29 or HCT116 cells were grown to near confluence and then serum starved 48 hrs at which point supernatants from cells were combined with trypsinized monolayers and cells. Cells ($1\times10^4$) were subjected to the Caspase 3/7 assay according the manufacturers instructions (Promega). Luminescence was measured as a quantification of caspase activity (Victor Wallac).

Figure 1:
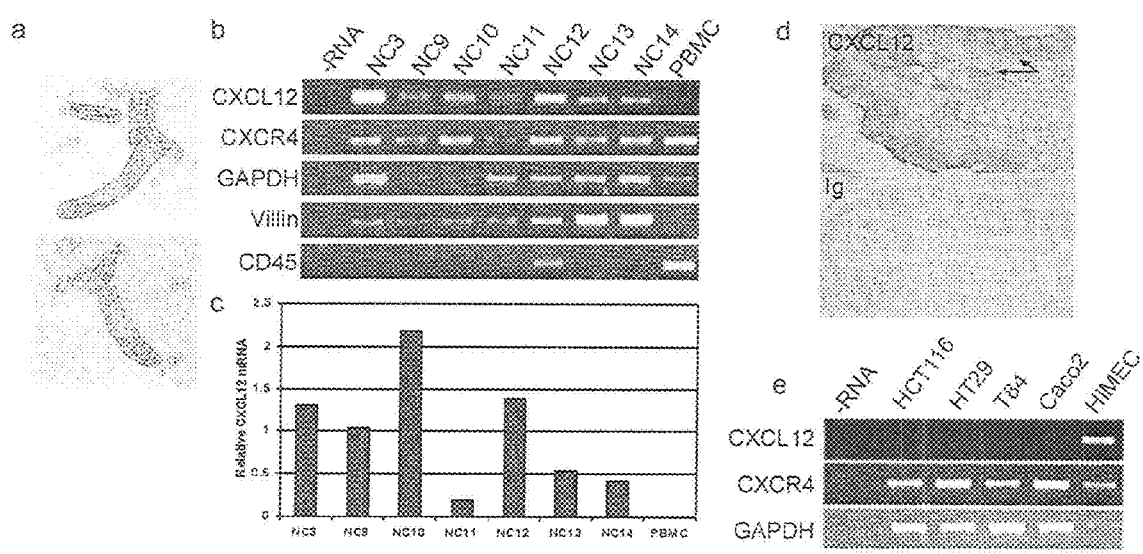
FIG. 1. Constitutive CXCL12 expression is absent in colonic carcinoma cell lines. (A) Representative samples of crypt and epithelial sheet preparations from normal human colonic mucosa. (B) CXCL12 and CXCR4 mRNA is expressed in normal crypt (NC) epithelium from seven separate surgical specimens. Epithelial enrichment was verified by RT-PCR amplification of villin. Mucosal leukocyte contamination was assessed by RT-PCR amplification of CD45. GAPDH was amplified as a loading control. (C) CXCL12 mRNA expression normalized to GAPDH in isolated colonic epithelial preparations indicated consistent CXCL12 expression in the normal colon. (D) Immunohistochemistry showing areas of CXCL12 staining (arrows) in normal colonic surface epithelium relative to isotype antibody control staining (Ig). (E) CXCL12 mRNA expression in HT29, HCT116, Caco2 and T84 colonic carcinoma cell lines was not detectable using RT-PCR analysis. cDNA derived from human intestinal microvascular endothelium (HIMEC) was used as a positive control. Data in A-E are representative of 2-3 independent analyses.

Constitutive CXCL12 expression in the human colonic epithelium is absent in colonic carcinoma cells. To establish CXCL12 expression in the colonic mucosa we isolated the crypt epithelium from resectioned human colonic tissue (FIG. 1a). RT-PCR analysis of these colonic crypts showed that both CXCL12 and CXCR4 were expressed by normal human colonic epithelium (FIGS. 1b and 1c). Immunohistochemistry verified CXCL12 protein expression in human colonic epithelium (FIG. 1d) indicating that CXCL12 mRNA expression did not reflect altered gene regulation resulting from crypt isolation (Agace, W. W., Amara, A., Roberts, A. I., Pablos, J. L., Thelen, S., Uguccioni, M., Li, X. Y., Marsal, J., Arenzana-Seisdedos, F., Delaunay, T., Ebert, E. C., Moser, B., and Parker, C. M. (2000). Constitutive expression of stromal derived factor-1 by mucosal epithelia and its role in HIV transmission and propagation. Curr. Biol. 10, 325-328). In agreement with our prior data CXCR4 protein expression was similarly observed in isolated crypts from human colonic tissues (data not shown). Isolated human peripheral blood monocytes (PBMC) assayed as a control did not express CXCL12 (Kimura, R., Nishioka, T., and Ishida, T. (2003). The SDF1-G801A polymorphism is not associated with SDF1 gene expression in Epstein-Barr virus-transformed lymphoblastoid cells. Genes Immun. 4, 356-361). Those data, combined with the amplification of villin and CD45 as control transcripts, indicate that CXCL12 and CXCR4 mRNA expression observed in our mucosal preparations solely reflected epithelial expression and was not the result of contaminating immune cells.

In marked contrast to normal colonic epithelium, CXCL12 was minimally, if at all, expressed in HT29, HCT116, Caco2, and T84 colonic carcinoma cell lines assessed using identical RT-PCR conditions as those used for normal samples (FIG. 1e). However, as a positive control, CXCL12 mRNA was expressed in human intestinal microvascular endothelial cells (HIMEC) (Heidemann, J., Ogawa, H., Rafiee, P., Lugering, N., Maaser, C., Domschke, W., Binion, D. G., and Dwinell, M. B. (2004). Mucosal angiogenesis regulation by CXCR4 and its ligand CXCL12 expressed by human intestinal microvascular endothelial cells. Am. J. Physiol Gastrointest. Liver Physiol 286, G1059-G1068). In contrast to CXCL12, CXCR4 was consistently expressed in both normal colonic epithelium and colonic carcinoma cell lines (FIGS. 1b and 1e) (Heidemann, J., Ogawa, H., Rafiee, P., Lugering, N., Maaser, C., Domschke, W., Binion, D. G., and Dwinell, M. B. (2004). Mucosal angiogenesis regulation by CXCR4 and its ligand CXCL12 expressed by human intestinal microvascular endothelial cells. Am. J. Physiol Gastrointest. Liver Physiol 286, G1059-G1068; Smith, J. M., Johanesen, P. A., Wendt, M. K., Binion, D. G., and Dwinell, M. B. (2005). CXCL12 activation of CXCR4 regulates mucosal host defense through stimulation of epithelial cell migration and promotion of intestinal barrier integrity. Am. J. Physiol Gastrointest. Liver Physiol 288, 316-26; Dwinell, M. B., Eckmann, L., Leopard, J. D., Varki, N. M., and Kagnoff, M. F. (1999). Chemokine receptor expression by human intestinal epithelial cells. Gastroenterology 117, 359-367). Taken together, these results suggest that CXCL12, unlike CXCR4 and other epithelial expressed chemokines (Izadpanah, A., Dwinell, M. B., Eckmann, L., Varki, N. M., and Kagnoff, M. F. (2001). Regulated MIP-3alpha/CCL20 production by human intestinal epithelium: mechanism for modulating mucosal immunity. Am. J. Physiol Gastrointest. Liver Physiol 280, G710-G719; Dwinell, M. B., Eckmann, L., Leopard, J. D., Varki, N. M., and Kagnoff, M. F. (1999). Chemokine receptor expression by human intestinal epithelial cells. Gastroenterology 117, 359-367), is significantly down-regulated in those human colonic carcinoma cell lines.

Identification of a putative CXCL12 promoter encompassed in a CpG island. We next sought to define the mechanism by which CXCL12 is specifically down-regulated in colonic carcinoma cells. The immediate 5' genomic region of CXCL12 lacks a true TATA-box and is rich in G/C content in the form of CpG dinucleotides, which is characteristic of homeostatic gene promoters (Shirozu, M., Nakano, T., Inazawa, J., Tashiro, K., Tada, H., Shinohara, T., and Honjo, T. (1995). Structure and chromosomal localization of the human stromal cell-derived factor 1 (SDF1) gene. *Genomics* 28, 495-500; Garcia-Moruja, C., Alonso-Lobo, J. M., Rueda, P., Torres, C., Gonzalez, N., Bermejo, M., Luque, F., Arenzana-Seisdedos, F., Alcami, J., and Caruz, A. (2005). Functional characterization of SDF-1 proximal promoter. *J. Mol. Biol.* 348, 43-62). Using promoter prediction software (Scherf, M., Klingenhoff, A., and Werner, T. (2000). Highly specific localization of promoter regions in large genomic sequences by PromoterInspector™: a novel context analysis approach. *J. Mol. Biol.* 297, 599-606) we examined 10 kb of genomic sequence encompassing the CXCL12 gene, including 2 kb of sequence upstream of the 5'-UTR. We identified an area of sequence extending from −493 to +168 as a putative promoter region, relative to transcriptional start, +1 (FIG. 2a). Our identification of this region as the CXCL12 promoter by computational analysis was recently verified experimentally (Garcia-Moruja, C., et al. (2005) *J. Mol. Biol.* 348, 43-62). Using CpG analysis software we determined that this promoter was surrounded by a large CpG island extending from −840 to +852 (Li, L. C. and Dahiya, R. (2002). *Bioinformatics.* 18, 1427-1431) (FIG. 2a). Three additional CpG islands were also identified further upstream extending from −1877 to −1581, −1391 to −1231, and −1123 to −899 (not shown).

The CXCL12 promoter is hypermethylated in human colorectal carcinoma. Next, we used methylation-specific PCR (MSP) and bisulphite sequencing PCR to determine the methylation status of the CXCL12 promoter as a potential mechanism for its transcriptional repression in colorectal carcinoma cells (Herman, J. G., et al. (1996). *Proc. Natl. Acad. Sci. U.S.A* 93, 9821-9826; Clark, S. J., et al. (1994) *Nucleic Acids Res.* 22, 2990-2997). In agreement with its mRNA and protein expression in normal human colonic epithelium, the CXCL12 promoter region in normal colonic epithelial isolates was consistently homozygous unmethylated (FIG. 2b).

Methylation of the CXCL12 promoter was further examined by bisulphite sequencing PCR (BSSP). Nearly all CpG's from −275 to −35 were methylated in HCT116 and HT29 carcinoma cells. Caco2 cells showed methylation of five CpG dinucleotides from −211 to −177 while T84 cells were heterozygous methylated at two CpG's in the examined promoter region. These latter data suggest additional sites of methylation or other mechanisms of gene silencing may also play a role in CXCL12 transcriptional regulation in those cell lines. In marked contrast to the carcinoma cell lines, this region of the promoter was consistently unmethylated in CXCL12-expressing normal epithelial samples and cultured HIMEC.

Promoter methylation and repression of epithelial CXCL12 protein expression in primary colonic carcinoma. Next, we used our diagnostic MSP to analyze the methylation status of the CXCL12 promoter in several primary colorectal carcinoma tissues to ensure hypermethylation was not solely a property of colonic carcinoma cell lines. Aberrant hypermethylation of the CXCL12 promoter was readily observed with increasing frequency in several carcinomas, but not normal mucosa, suggesting chemokine gene silencing during in vivo disease progression (FIG. 2b and FIG. 2c). Consistent with the heterogeneous nature of colorectal tumors, we determined that hypermethylation of the CXCL12 promoter was observed in more than half of the colorectal tumors analyzed by MSP, with 62% of 21 separate colonic carcinomas possessing methylated CXCL12 alleles (FIG. 2c). Moreover, our observed frequency for CXCL12 methylation is consistent with other genes previously shown to be silenced by DNA hypermethylation and involved with cancer in vivo (Robertson, K. D. (2001) *Oncogene* 20, 3139-3155).

Carcinomas determined to contain methylated alleles of CXCL12 were further analyzed by immunohistochemistry to define CXCL12 protein expression in cancerous versus normal human colonic mucosa. As shown in FIG. 2d for a representative sample, CXCL12 was not detectable in the disorganized cancerous epithelium, while adjacent regions of organized normal epithelium maintained expression of that homeostatic chemokine. Parallel sections of the same tissues indicated that both the normal, CXCL12-expressing, and dysplastic, CXCL12-null, epithelium expressed CXCR4 (FIG. 2d). Taken together these results suggest that methylation of the CXCL12 promoter is a pathological event in vivo and may play a role in its transcriptional repression in human colorectal carcinoma.

Figure 3:
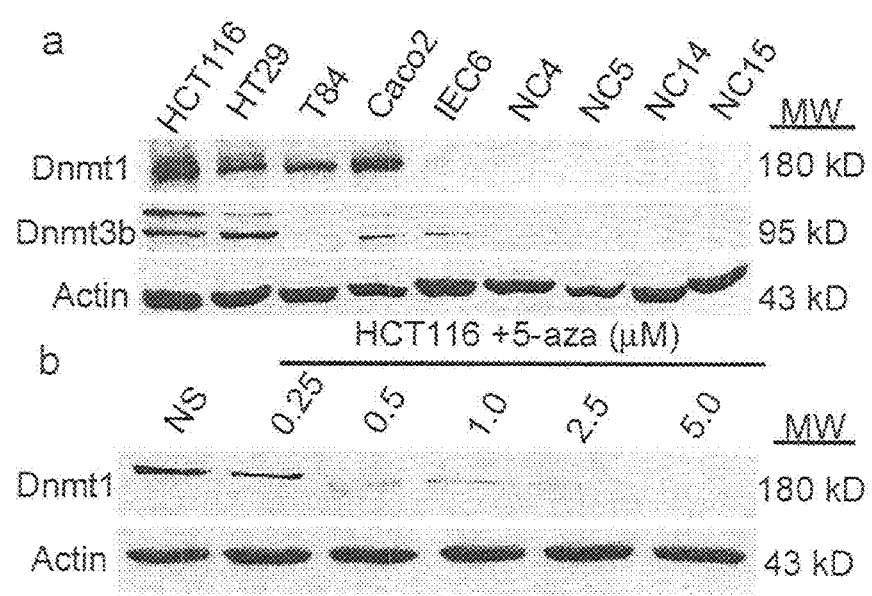
FIG. 3. DNA methyltransferase-1 (Dnmt1) and Dnmt3b are over-expressed in colonic carcinoma cell lines. (A) Immunoblot analysis showing Dnmt1 and Dnmt3b expression in the CXCL12-null HCT116, HT29, T84, and Caco2 cells compared to CXCL12-expressing normal colonic (NC) epithelial preparations and cultured non-transformed IEC6 cells. (B) Immunoblot analysis showing extractability of Dnmt1 was inhibited in HCT116 cells treated with increasing concentrations of 5-aza. Levels of Actin indicated equal protein loading between non-stimulated (NS) and 5-aza-treated HCT116 cells. Data in A-B are representative of 3 independent experiments.

Dnmt enzymes are over-expressed in colorectal carcinoma cell lines. To better define the mechanism leading to CXCL12 hypermethylation in colonic carcinoma cells we determined Dnmt expression in those cells as compared to normal epithelium. Consistent with CXCL12 promoter hypermethylation, HCT116, HT29, T84 and Caco2 colonic carcinoma cell lines strongly expressed Dnmt enzymes. In sharp contrast, the proteins were not detectable in normal mucosal samples or the IEC6 cell line, a model of normal non-transformed intestinal epithelium (FIG. 3a). Importantly, the extractable levels of Dnmt 1 could be mechanistically ablated by the Dnmt inhibitor, 5-aza-2'-deoxycytidine (5-aza) (FIG. 3b) (Jones, P. A. and Taylor, S. M. (1980) *Cell* 20, 85-93).

Figure 4:
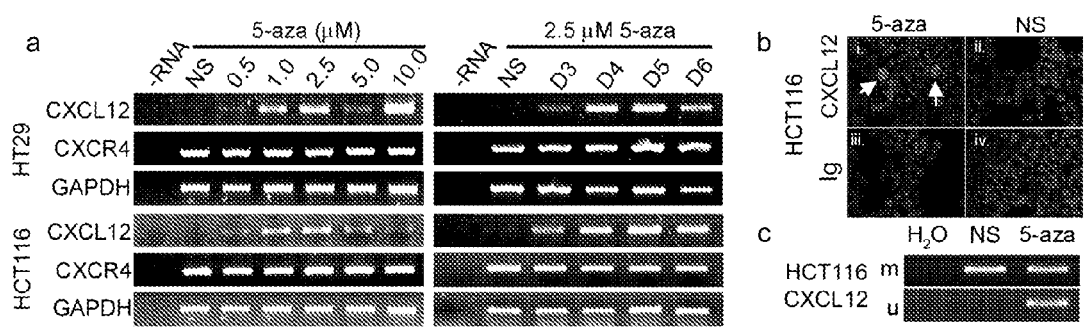
FIG. 4. Inhibition of DNA methyltransferase (Dnmt) enzymes restored CXCL12 expression. (A) Treatment of HT29 (top) and HCT116 (bottom) cells with the indicated concentrations of 5-aza for five days or with 2.5 µM 5-aza for 3, 4, 5, or 6 days (D3-D6) resulted in re-expression of CXCL12 relative to non-stimulated (NS) cells. CXCR4 mRNA levels remained unchanged with 5-aza treatment. GAPDH was amplified as a loading control. (B) Immunofluorescence analysis indicated the recovery of CXCL12 specific staining (see arrows) after 3 days of 2.5 µM 5-aza treatment (bi.). No CXCL12 specific staining was observed in non-stimulated control HCT116 cells (bii). IgG staining for 5-aza treated (biii.) and non-stimulated HCT116 cells (biv.) were performed to define levels of non-specific immunostaining. (C) CXCL12 methylation-specific PCR indicating the presence of unmethylated alleles of CXCL12 in HCT116 cells treated with 2.5 µM 5-aza for 3 days. Data in a-c are representative of 3 independent experiments.

Inhibition of Dnmt enzymes restores CXCL12 expression in colonic carcinoma cells. We next sought to determine whether inhibition of Dnmt enzymes could re-establish CXCL12 expression in colorectal carcinoma cells. Treatment of either HT29 or HCT116 colonic carcinoma cells with 5-aza dose-dependently restored CXCL12 mRNA expression (FIG. 4a). Furthermore, treatment of those cells with the optimal 2.5 µM concentration of 5-aza restored CXCL12 expression, with maximal re-expression noted after 5-days (FIG. 4a). Treatment of Caco2 and T84 cells with 5-aza, similarly fostered gene re-expression, suggesting that these heterozygous methylated cell populations harbor functional alleles of CXCL12 that are silenced by DNA hypermethylation (data not shown). In parallel with restored CXCL12 mRNA expression, protein expression was detected by immunofluorescence microscopy upon 5-aza treatment (FIG. 4b).

It has been suggested that CXCL12 expression can be enhanced by tissue and DNA damage (Ponomaryov, T., Peled, A., Petit, I., Taichman, R. S., Habler, L., Sandbank, J., Arenzana-Seisdedos, F., Magerus, A., Caruz, A., Fujii, N., Nagler, A., Lahav, M., Szyper-Kravitz, M., Zipori, D., and Lapidot, T. (2000). Induction of the chemokine stromal-derived factor-1 following DNA damage improves human stem cell function. *J. Clin. Invest* 106, 1331-1339). To ensure that 5-aza was restoring CXCL12 transcription by inhibiting methylation and not by nonspecific DNA damage, we used MSP to analyze DNA from 5-aza treated cells. Methylation of the CXCL12 promoter was inhibited by 5-aza treatment in HCT116 (FIG. 4c) and HT29 cells (data not shown). Taken together these data indicate that pharmacological Dnmt inhibition prevents methylation of the CXCL12 promoter and allows mRNA and protein expression in colonic carcinoma cells.

Figure 5:
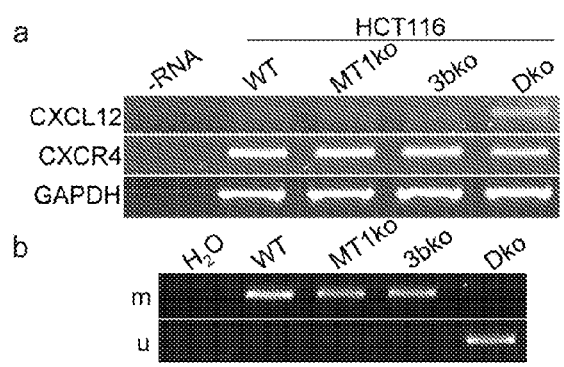
FIG. 5. CXCL12 expression in DNA methyltransferase (Dnmt)-deficient HCT116 carcinoma cells. (A) CXCL12 and CXCR4 mRNA expression analyzed by RT-PCR in wild-type, WT; Dnmt1 knockout, MT1ko; Dnmt3b knockout, 3bko; or Dnmt1/Dnmt3b double knockout, Dko HCT116 cells. (B) CXCL12 methylation-specific PCR analysis showing the DNA methylation profile of the Dnmt deficient HCT116 cells. CXCL12 is homozygous methylated in the WT parent, MT1ko and 3bko cells that lack CXCL12 mRNA transcripts. Dko cells that express the CXCL12 transcript were homozygous unmethylated. Data are representative of 3 independent experiments.

Dnmt1 and Dnmt3b silence CXCL12 in colorectal carcinoma cells. We next utilized HCT116 cells lacking Dnmt1 (MT1kO), Dnmt3b (3bkO), or both enzymes (Dko) to define the mechanism by which CXCL12 becomes silenced in colorectal cancer. Specific gene deficiency in these cell lines has previously been shown (Rhee, I., et al. (2002) *Nature* 416, 552-556) and was verified in our laboratory using RT-PCR and immunoblot analyses (data not shown). Consistent with CXCL12 being silenced by DNA hypermethylation the transcript was expressed in HCT116 cells lacking both Dnmt1 and Dnmt3b, but not the single knockout cell line (FIG. 5a). Further, MSP analysis showed that CXCL12 was homozygous unmethylated in Dko cells as opposed to the homozygous methylated profile of the wild-type parent, or similarly, the cells lacking only Dnmt1 or Dnmt3b (FIG. 5b). These data agree with the Dnmt expression and methylation patterns of our cultured cell lines and suggest that either Dnmt1 or Dnmt3b can silence CXCL12 expression in carcinogenic but not normal colonic epithelium.

Figure 6:
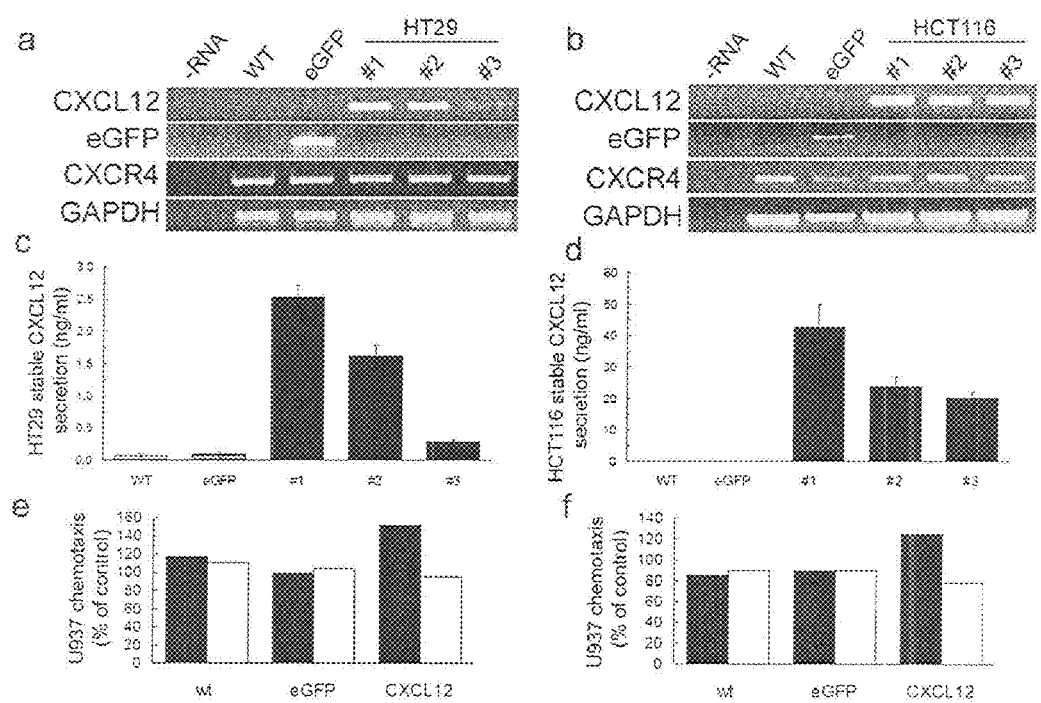
FIG. 6. Stable re-expression of functional CXCL12 in colonic carcinoma cells. (A-B) HT29 (A) and HCT116 (B) cells were stably transfected with plasmid vectors encoding CXCL12 or eGFP as a control and specific gene expression verified by RT-PCR. CXCR4 mRNA levels remained unchanged following re-expression of CXCL12. GAPDH was amplified as a loading control. (c-d) CXCL12 protein was detectable in the supernatant of several independent CXCL12 stable transfectant clones in both HT29 (C) and HCT116 (D) cells, but not the WT or vector control cell lines. (E-F) CXCL12 produced by HT29 (E) and HCT116 (F) cells stimulated the chemotaxis of CXCR4-expressing U937 monocytic cells (black bars). Chemotaxis was specifically inhibited by the CXCR4 antagonist AMD3100 (5 μg/ml) (white bars). Data are representative of 3 independent experiments.
Figure 7:
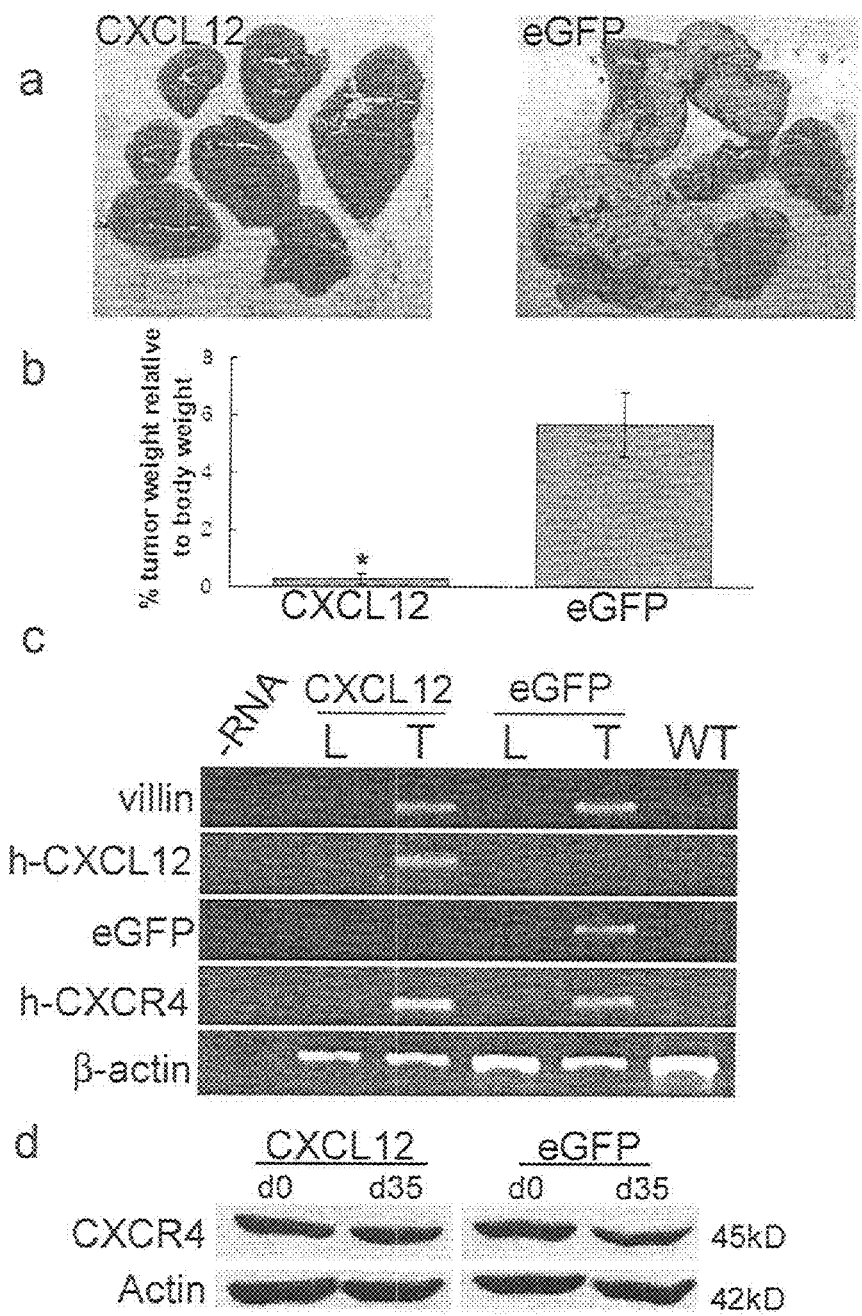
FIG. 7. Endogenous CXCL12 expression in CXCR4-expressing colonic carcinoma cells reduced in vivo metastatic tumor formation in SCID mice. (A) CXCL12 or eGFP-expressing HT29 human colonic carcinoma cells were injected into the hepatic portal vein of SCID mice and allowed to form metastases for five weeks. eGFP-expressing carcinoma cells formed noticeably larger metastases (white tissue) than did CXCL12-expressing HT29 cells. Data are representative of five separate mice per treatment group. (B) Tumors dissected from normal liver tissue were weighed and data presented as percent of body weight. Asterisk equals significant decrease in tumor size ($P \leq 0.05$) between tumors resulting from CXCL12 stable carcinoma cells and those of the eGFP vector control cells. Data in panel B are mean±SD of 5 separate mice per group. (C) RT-PCR analyses of the dissected tumor fractions (T) were positive for villin, a marker of intestinal epithelial cells, while normal liver tissue (L) lacked villin expression similar to wild-type (WT) mouse liver tissue from a non-injected animal. In vivo transgene expression of human CXCL12 (h-CXCL12) and eGFP were verified for each of the two tumor types. (D) Immunoblot analysis showing consistent CXCR4 expression in CXCL12 and eGFP expressing HT29 cells both before (d0) and after tumor dissection 35 days following injection into SCID mice (data representative of three separate mice per treatment group).

Endogenous CXCL12 expression by colonic carcinoma cells decreases metastatic tumor formation. Having established an epigenetic mechanism for CXCL12 silencing in human colorectal carcinoma, we sought to define the significance of this event in disease progression. We therefore generated HT29 and HCT116 colonic carcinoma cells which stably expressed CXCL12 in order to recapitulate the CXCR4 signaling axis of the normal colonic epithelium (Dwinell, M. B., et al. (1999) *Gastroenterology* 117, 359-367). RT-PCR analysis showed specific expression of CXCL12 or eGFP used as a vector control, in both HT29 and HCT116 carcinoma cells (FIGS. 6A and 6B). CXCR4 mRNA expression (FIGS. 6a and 6b) and total protein levels were comparable in the wild-type parent cell lines, CXCL12 expressing, and vector control cells (FIG. 7d). CXCL12 protein was detected in the supernatant of CXCL12 transfected HT29 and HCT116 colonic carcinoma cells, but not parent or vector control cells, and was within the normal physiological range for that chemokine (FIGS. 6C and 6D) (Derdeyn, C. A., et al. (1999) *AIDS Res. Hum. Retroviruses* 15, 1063-1071). Further, CXCL12 secreted from both HT29 and HCT116 stable transfectants was functional, as assessed by the ability to stimulate chemotaxis of CXCR4-expressing U937 monocytic cells (FIGS. 6e and 6f). Further, chemotaxis of those cells was specific for epithelial CXCL12-leukocyte CXCR4 as the receptor antagonist AMD3100 potently blocked migration of those cells across the filter (FIGS. 6e and 6f).

To determine the in vivo impact of endogenous CXCL12 expression on colonic carcinoma disease progression we utilized a SCID mouse model of tumor cell metastasis (Panis, Y., et al. (1990) *J. Hepatol.* 11, 53-57). Carcinoma cells stably re-expressing CXCL12 or control eGFP cells were injected into the portal vein to assess the ability of those cells to invade and colonize the liver. Consistent with the notion that CXCL12 silencing aids in carcinoma cell metastasis, colon carcinoma cells in which CXCL12 was endogenously re-expressed formed significantly smaller metastatic lesions than did eGFP-expressing vector control cells (FIGS. 7a and 7b). Resultant dissected metastatic tumors from mice injected with CXCL12 stable cell lines maintained expression of human CXCL12 as verified using RT-PCR (FIG. 7c). However, CXCL12 expression was absent in those tumors resulting from the eGFP vector control. The native CXCL12 locus remained methylated in resultant tumors for all cases (data not shown). Primers specific for the human villin transcript were used as a marker for the presence of intestinal epithelial cells in the developed tumors and was absent in both dissected normal liver and wild-type non-injected liver tissue (FIG. 7c). Further, CXCR4 expression in HT29 stable CXCL12 and eGFP carcinoma cells (FIGS. 7c and 7d) was maintained at comparable levels was not significantly altered after implantation into SCID mice. These data were not unique to HT29 cells as our HCT116 cells stably re-expressing CXCL12 (FIG. 6) formed similar small metastatic tumors relative to the control cells in SCID mice (data not shown).

Figure 8:
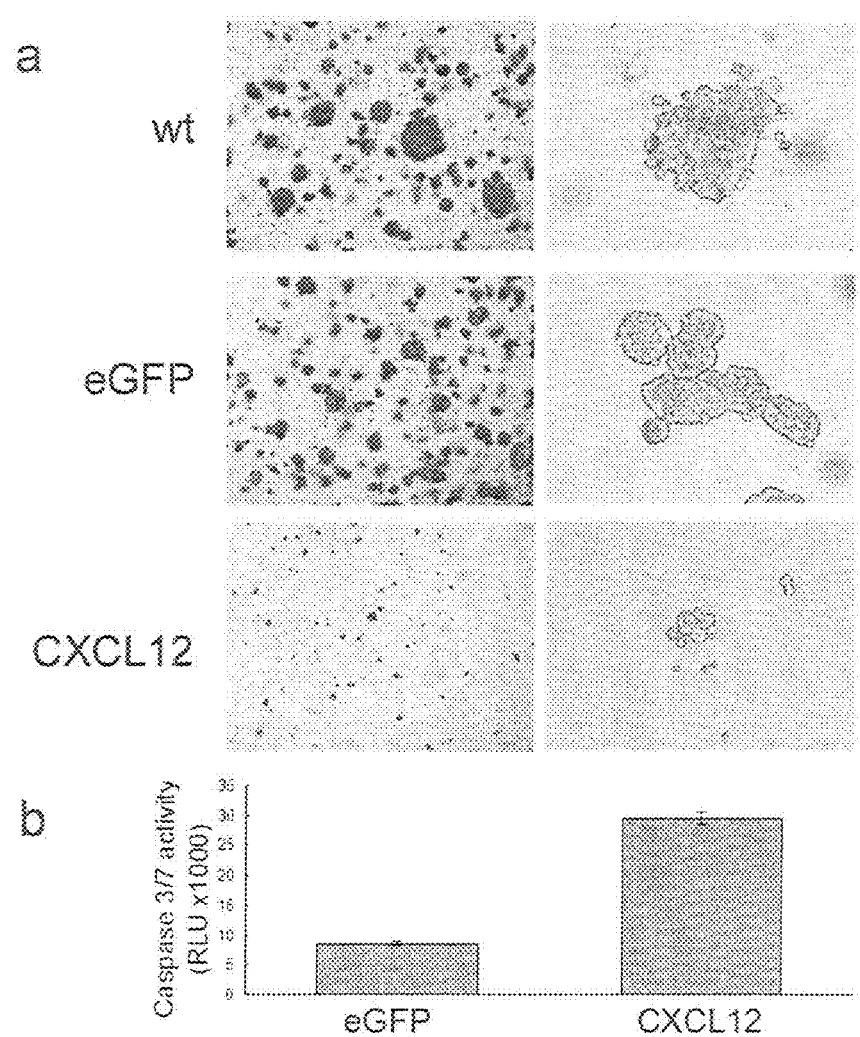
FIG. 8. Endogenous CXCL12 secretion by colonic carcinoma cells reduces in vitro soft agar foci formation and increases caspase 3/7 activity. (A) HT29 cells stably transfected with CXCL12 form smaller foci when grown two weeks in soft agar as compared to vector control (eGFP) or wild-type (WT) parent cells. Brightfield microscopy images at 40× (left) and 200× (right). (B) eGFP or CXCL12-expressing HT29 cells ($1 \times 10^4$) were analyzed using a Caspase 3/7 luminescence assay. Data were expressed as relative luciferase units (RLU) and showed greater caspase activity in CXCL12-expressing cells than eGFP cells. Images in (A) are representative of three independent experiments. Values in (B) are the mean±SD of replicate samples and representative of three independent experiments.

We next sought to define possible biochemical mechanisms preventing in vivo metastatic tumor formation by colonic carcinoma cells in which CXCL12 was re-established. In agreement with our SCID mouse model, several clones of HT29 cells stably re-expressing CXCL12 failed to invade the matrix and establish foci in soft-agar (FIG. 8a). The inability of CXCL12 stable transfectants to form foci suggested a decreased ability of CXCL12 expressing cells to invade and populate their surrounding microenvironment. Consistent with this notion we observed an increase in apoptosis in CXCL12 expressing cells compared to eGFP clones, as assessed by active caspase-3/7 levels (FIG. 8b). HCT116 cells stably expressing CXCL12 similarly had increased caspase 3/7 activity (not shown). Together, these data suggest that autocrine CXCL12-CXCR4 signaling, a process subverted by colon cancer cells through the silencing of CXCL12, increases caspase 3/7 activity inhibiting the ability of carcinoma cells to metastasize in vivo.

We claim:

1. A method of treating colon carcinoma exhibiting reduced or silenced CXCL12 protein expression in a patient, the method comprising administering to the patient a therapeutically effective amount of CXCL12 protein.

2. The method of claim 1 wherein the method of administration of CXCL12 is via native protein.

3. A method of treating carcinoma exhibiting reduced or silenced CXCL12 protein expression in a patient, the method comprising administering to the patient a therapeutically effective amount of CXCL12 protein.

4. The method of claim 3 wherein the method of administration of CXCL12 is via native protein.

* * * * *